(12) United States Patent
Vartiovaara

(10) Patent No.: US 11,281,869 B2
(45) Date of Patent: Mar. 22, 2022

(54) METHODS AND DEVICES FOR DEVICE DETECTION USING MAGNETIC SIGNATURES

(71) Applicant: General Electric Company, Schenectady, NY (US)

(72) Inventor: Ville Petteri Vartiovaara, Tuusula (FI)

(73) Assignee: General Electric Company, Schenectady, NY (US)

( * ) Notice: Subject to any disclaimer, the term of this patent is extended or adjusted under 35 U.S.C. 154(b) by 186 days.

(21) Appl. No.: 16/231,236

(22) Filed: Dec. 21, 2018

(65) Prior Publication Data
US 2020/0202083 A1 Jun. 25, 2020

(51) Int. Cl.
*G06K 7/08* (2006.01)
*A61B 5/0205* (2006.01)
(Continued)

(52) U.S. Cl.
CPC .......... *G06K 7/087* (2013.01); *A61B 5/02055* (2013.01); *A61B 5/021* (2013.01); *A61B 5/0809* (2013.01); *A61B 5/14551* (2013.01); *A61B 5/25* (2021.01); *A61B 5/291* (2021.01); *A61B 2562/226* (2013.01)

(58) Field of Classification Search
CPC ................ G06K 7/087; H01R 13/6205; A61B 2562/08; A61B 2562/226; A61B 2562/02055; A61B 2562/021; A61B 2562/0408; A61B 2562/0478; A61B 2562/0809; A61B 2562/14551; A61B 2562/045; A61B 2562/0214; A61B 2562/0271; A61B 2562/0276; A61B 2562/6826; A61B 2562/0205
See application file for complete search history.

(56) References Cited

U.S. PATENT DOCUMENTS 5,543,988 A * 8/1996 Brady .................... G01R 33/06
257/421
2002/0188181 A1* 12/2002 Boit ...................... G06F 1/1632
600/300
(Continued)

FOREIGN PATENT DOCUMENTS

WO 2017036935 A1 3/2017

OTHER PUBLICATIONS

PCT application PCT/US2019/067723 filed Dec. 20, 2019; International Search Report/Written Opinion dated Apr. 2, 2020, 17 pages.

*Primary Examiner* — Nathan J Jenness
(74) *Attorney, Agent, or Firm* — McCoy Russell LLP

(57) ABSTRACT

Various methods and devices are provided for detecting a device connection based on a magnetic signature. In one example, a host device includes a connector configured to connect to a medical sensor device, a magnetic detection unit positioned proximate the connector and including a magnetic field generator and one or more magnetic field detectors, and a memory storing instructions executable by a processor to determine a magnitude of a magnetic field generated by the magnetic field generator based on output from the one or more magnetic field detectors and in response to detecting a change in the magnitude of magnetic field that is greater than a threshold change, establish a connection with the medical sensor device.

18 Claims, 11 Drawing Sheets

(51) Int. Cl.

| | |
|---|---|
| *A61B 5/021* | (2006.01) |
| *A61B 5/08* | (2006.01) |
| *A61B 5/1455* | (2006.01) |
| *A61B 5/25* | (2021.01) |
| *A61B 5/291* | (2021.01) |

(56) References Cited

U.S. PATENT DOCUMENTS

| | | | |
|---|---|---|---|
| 2005/0014526 A1* | 1/2005 | Pan | H04M 1/7246 |
| | | | 455/550.1 |
| 2007/0072443 A1* | 3/2007 | Rohrbach | G06F 1/18 |
| | | | 439/39 |
| 2012/0001751 A1* | 1/2012 | Baker | A61B 5/7285 |
| | | | 340/539.12 |
| 2017/0264045 A1 | 9/2017 | Eslava | |
| 2017/0303990 A1* | 10/2017 | Benamou | A61B 18/1442 |
| 2017/0325684 A1 | 11/2017 | Vartiovaara | |

* cited by examiner

METHODS AND DEVICES FOR DEVICE DETECTION USING MAGNETIC SIGNATURES

FIELD

Embodiments of the subject matter disclosed herein relate to devices and methods for detecting the attachment of a medical sensor device to a host device.

BACKGROUND

Medical sensor devices are widely used in care delivery areas such as patient monitoring and fetal monitoring for monitoring physiological conditions of patients or fetuses, such as electrocardiography (ECG), electroencephalograph (EEG), blood pressure, temperature, heart rate, oxygen saturation, etc. A medical sensor device may be connected to a host device, which can supply power to the sensor device for operation and receive physiological data acquired by the sensor device. The host device can process the physiological data, display the physiological condition for review, and/or transmit the physiological data to a remote processing/storage system.

BRIEF DESCRIPTION

In one embodiment, a host device includes a connector configured to connect to a medical sensor device, a magnetic detection unit positioned proximate the connector and including a magnetic field generator and one or more magnetic field detectors, and a memory storing instructions executable by a processor to determine a magnitude of a magnetic field generated by the magnetic field generator based on output from the one or more magnetic field detectors and in response to detecting a change in the magnitude of magnetic field that is greater than a threshold change, establish a connection with the medical sensor device.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
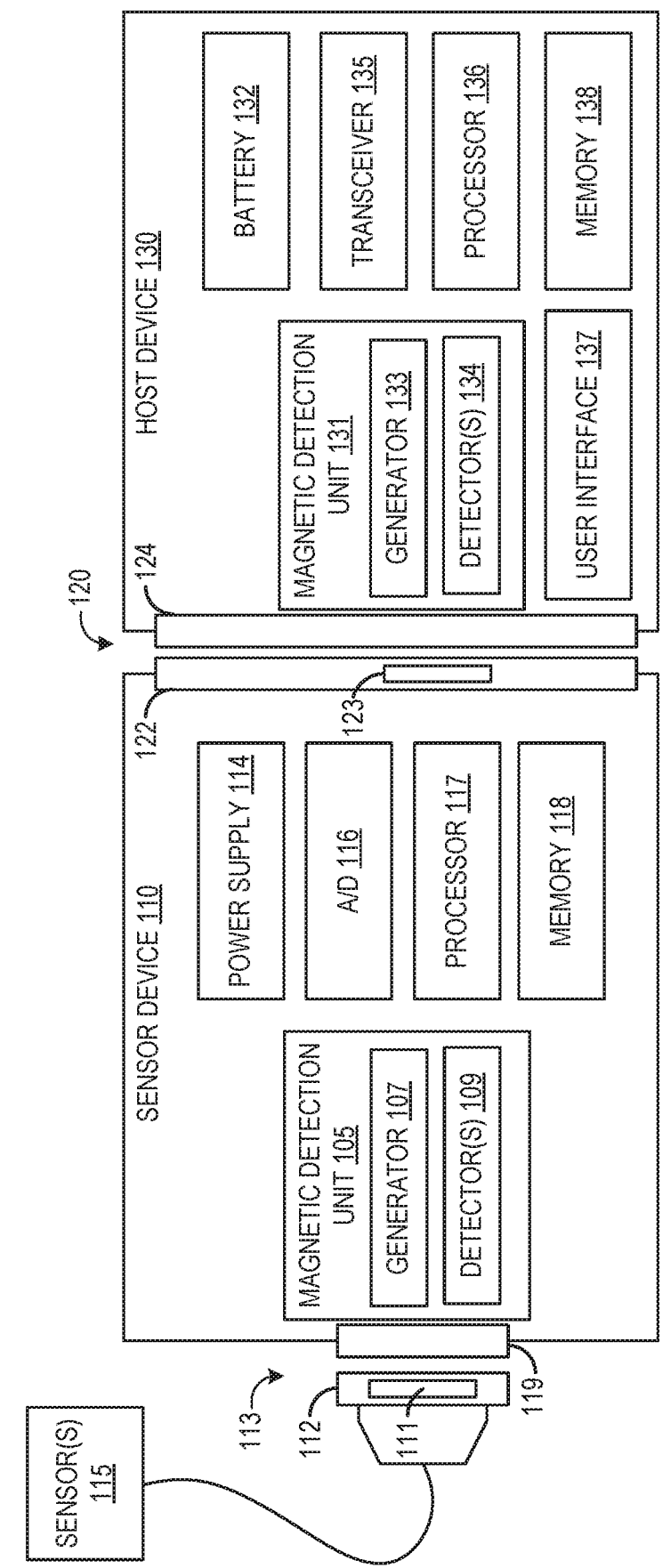
FIG. 1 is a block diagram of a medical sensor device and a host device in accordance with an embodiment of the present disclosure.

The following description relates to various embodiments of detecting a connection between a host device and a sensor device and/or detecting a connection between a sensor device and a sensor. When the sensor device is being attached to the host device, the host device may detect the presence of the sensor device and react by, for example, initiating a handshake sequence with the sensor device and/or turning on the power to the sensor device, thereby establishing the power/communication connection with the sensor device. Further, it may be desirable for the host device to detect which type of sensor device has been connected. When waiting for this event, there may be limited amount of energy available in the host device. Further, the unconnected interface may pose risks to patients if an amount of power used to detect the presence of the sensor device is too high. Mechanical switches and optical detectors have been used to detect the attachment of the sensor device. However, mechanical switches are prone to wear out or stalling. Optical detectors may add complexity and cost to the patient monitoring system. Further, traditional magnetic switches require strong static magnetic fields that may be hazardous or collect ferromagnetic debris.

Thus, according to embodiments disclosed herein, a detection mechanism may be provided that is low power, safe to the patient, low cost, and has no moving parts. The detection mechanism described herein includes one or more magnetic field detectors and a magnetic field generator on the host device and one or more magnetic signatures on the sensor device (e.g., the magnetic signature may be a magnetizable part having a certain size, shape, etc.). The magnetic field detector(s) may detect a change in the magnetic field due to the presence of the magnetic signature when the sensor device is connected to the host device. In some examples, the sensor device, via the magnetic signature, may convey additional information to the host device. For example, different sensor devices may have different magnetic signatures. Further, any risks related to mis-use or other rare events resulting in a magnetic signature being detected without a sensor device actually being connected may be mitigated by a secondary handshake. The detection mechanism described herein provides a low-power robust first-level detection comparable to a mechanical actuation switch or similar.

The present disclosure provides devices and methods for detecting a medical sensor device being attached to a host device. The medical sensor device may include an ECG monitor, EEG monitor, non-invasive blood pressure (NIBP) monitor, pulse oximeter, temperature monitor, or any suitable device for monitoring physiological conditions of a patient or a fetus. The host device may supply power to the medical sensor device for operation and the host device may receive physiological data acquired by the sensor device. The sensor device may be connected to the host device through an interface, which includes a connector at the sensor device side and a connector at the host device side. The host device includes a magnetic detection unit that includes a magnetic field generator that may generate a weak magnetic field localized at the magnetic detection unit and one or more magnetic field detectors that may detect the magnetic field. When the sensor device is attached to the host device, the magnetic field at the magnetic detection unit may change due to the proximity of a magnetizable part disposed on or embedded within the sensor device. The host device compares the magnitude of the magnetic field change with an expected change. If the magnitude of the magnetic field change within a threshold range of the expected change, the host device determines that the sensor device is present and establishes a connection with the sensor device. Additional information may also be communicated to the host device via the magnetizable part of the sensor device. For example, the magnetizable part may have a given size, shape, distribution, location, etc., that may affect the magnetic field in a known way, and the manner in which the magnetizable part affects the magnetic field may be associated with the additional information. The additional information may include sensor type, sensor manufacturer, sensor orientation, and so forth.

The above-described magnetic detection method is safe to a patient, does not cause excessive leakage current, and has a high specificity and sensitivity. In addition, the detection method is low-cost and reliable because no moving parts are used.

Now referring to FIG. 1, a block diagram of a sensor system 100 that includes a medical sensor device 110 and a host device 130 is shown, in accordance with an exemplary embodiment. As illustrated in FIG. 1, in some embodiments, the sensor device 110 and the host device 130 may be connected through an interface 120, which includes a first connector 122 at the sensor device side and a second connector 124 at the host device side. In some embodiments, the interface 120 may transfer power from the host device 130 to the sensor device 110. In some embodiments, the interface 120 may communicate data between the sensor device 110 and the host device 130.

As illustrated in FIG. 1, in some embodiments, the medical sensor device 110 includes first connector 122, a power supply 114, an analog-to-digital (A/D) converter 116, a processor 117, and a memory 118. The sensor device 110 is configured to couple to one or more sensors 115. The one or more sensors 115 may include any sensor(s) 115 for sensing patient/fetal physiological conditions. For example, the sensor device 110 may be an ECG monitor wherein the sensor(s) 115 include ECG electrodes. The sensor device 110 may be an EEG monitor wherein the sensor(s) 115 include EEG electrodes. The sensor device 110 may be a NIBP monitor wherein the sensor(s) 115 include a blood pressure sensor. The sensor device 110 may be a peripheral oxygen saturation (SpO2) monitor wherein the sensor(s) 115 include a pulse oximeter. The sensor device 110 may be a temperature monitor wherein the sensor(s) 115 include a thermometer. The one or more sensors 115 may connect to the sensor device 110 via an interface 113 that includes a connector 112 of the sensor and a connector 119 of the sensor device. When connected, the interface 113 may transfer power from the sensor device 110 to the one or more sensors 115. Further, the interface 113 may communicate data between the sensor device 110 and the one or more sensors 115.

In some embodiments, the sensor device 110 may be attached to a patient by various mechanism so that the device can be worn or maintained on or near the patient. For example, an ECG monitor may be attached to a patient via a chest strap or a waist strap. An EEG monitor may be attached to a patient by a headband, neckband, chest band, or armband, or may be attached directly to an ECG electrode or a separate accessory adhered to the skin of the patient. A NIBP monitor may be attached to a cuff which may be worn by the patient. A pulse oximeter may be attached to a wristband which may be worn by the patient. In some embodiments, the sensor device 110 may be disposable for hygienic purposes.

The A/D converter 116 may digitize the physiological signals acquired by the sensor(s) 115. The A/D converter 116 may be any device or logical set capable of digitizing analog signals. In some embodiments, the A/D converter 116 includes an Analog Front End (AFE).

In some embodiments, the sensor device 110 includes a processor 117 which receives the digital physiological data from the A/D converter 116 and transmits the data to the host device 130 via the interface 120. In addition, the processor 117 may be configured to perform various functions, depending on the type of sensor(s) 115 and/or sensor device 110. The sensor device 110 includes a memory 118 storing instructions that are executable by the processor 117 in order to carry out the functions. For example, if the sensor device 110 is an ECG monitor and the sensor(s) 115 include ECG electrodes, the memory 118 may include instructions executable by the processor 117 to determine a heart rate. If the sensor device 110 is an EEG monitor and sensor(s) 115 include EEG electrodes, the memory 118 may include instruction executable by the processor 117 to determine a depth of anesthesia measurement value, such as an entropy value or a sedation responsiveness index value. If the sensor device 110 is a blood pressure monitor and the sensor(s) 115 includes a blood pressure sensor, the memory 118 may include instructions executable by the processor 117 to calculate systolic, diastolic and/or mean blood pressure values. If the sensor device 110 is an SpO2 monitor and the sensor(s) 115 include a pulse oximeter, the memory 118 may store instructions executable by the processor 117 to determined blood oxygenation value. Further, in some examples, the processor 117 may be configured to control operation of the sensor(s) 115. For example, if the sensor(s) 115 include a pulse oximeter, the memory 118 may include instructions executable by the processor 117 to control a frequency and/or intensity of light output by the light emitters of the pulse oximeter.

In some embodiments, the sensor device 110 does not include a processor. For example, if the sensor(s) 115 include a thermometer for sensing a patient's temperature, the sensor device 110 may be a relatively simple device without a processor. In addition, the temperature sensor device may be disposable, thus it would be cost efficient not to include a processor. In this case, the A/D converter 116 sends the digital physiological data to the host device 130 via the interface 120.

The power supply 114 supplies power to the sensor(s) 115, A/D converter 116, and processor 117. In some embodiments, the power supply 114 includes conductors that conduct power received from the host device 130 via the interface 120. In some embodiments, the power supply 114 includes a battery that is charged by the host device 130 via the interface 120 and distributes power to the various components of the sensor device 110. In further embodiments where the sensor device 110 involves demanding electromechanical functions (e.g., NIBP sensing), the power supply 114 has power management capabilities.

It should be understood that the medical sensor device 110 as shown in FIG. 1 is for illustration not for limitation. Any suitable sensor device may be used, which may have more, fewer, and/or different components than what are shown in FIG. 1.

In some embodiments, the host device 130 is a device that relays information between the sensor device 110 and a remote processing system, such as a central monitoring station and/or a central storage location (not shown in FIG. 1), via a wireless connection, such as antenna or access point. The central monitoring station provides a central location for clinicians to monitor patient status and/or receive alarm notifications. In some embodiments, the central monitoring station includes a local network with servers housed within a medical facility. In some embodiments, the central monitoring station includes a cloud-based system hosted by a cloud computing provider. The central storage location can store patient information which may be part of a patient's medical record and may be accessible by clinicians. In some examples, the host device 130 may relay the information between the sensor device 110 and the remote processing system via a patient monitoring hub, which may be a wireless enabled device located proximate the host device 130 (e.g., in the same room).

In some embodiments, the host device 130 is a device that relays information between the sensor device 110 and a transceiver proximate to the patient (not shown in FIG. 1) via a wireless connection. The proximate transceiver communicates with a remote processing system (e.g., central monitoring station, central storage location) via a wireless connection. For example, the host device 130 may be a generic activator module that is configured to be connected to various types of sensor devices. For example, the host device 130 may connect to an ECG monitor (e.g., when sensor device 110 is in the form of an ECG monitor as described above). When the ECG monitor is removed, the host device 130 may be coupled to a pulse oximeter (e.g., when another sensor device 110 is in the form of a pulse oximeter, as described above).

As illustrated in FIG. 1, in some embodiments, the host device 130 includes a battery 132, transceiver/transmitter 135, processor 136, user interface 137, and memory 138. The processor 136 receives the digital physiological data transmitted from the sensor device 110 via the interface 120. In some embodiments, the processor 136 is further configured to process the digital physiological data. For example, the memory 138 may store instructions executable by the processor 136 to determine the type of the sensor device 110 to which the host device 130 is connected and process the data based on the type of the sensor device 110.

The processor 136, according to instructions stored in memory 138, operates a transceiver or transmitter 135 to transmit data to a remote or proximate processing system, where the data may be further processed, stored, and/or transmitted. In some examples, the transceiver or transmitter 135 (for the simplicity of expression, transceiver is used herein to include both transceiver and transmitter) may communicate with (e.g., transmit data to) a patient monitoring hub, which may be located proximate the host device 130 (e.g., in the same room). The patient monitoring hub may then communicate with (e.g., transmit data to) a processing system that may be remote or proximate the patient monitoring hub. One or both of the patient monitoring hub and processing system may include a user interface, such as a display screen, to present the data from the host device to one or more users. The transceiver 135 may include any device for wirelessly transmitting data. In some embodiments, the transceiver 135 uses protocols for body area network (BAN), such as medical body area network (MBAN), used by wearable or portable computing devices. In some embodiments, the transceiver 135 uses protocols for wireless medical telemetry service (WMTS) or a Wi-Fi compliant wireless local area network (WLAN). In some embodiments, the transceiver 135 uses protocols for Bluetooth, Bluetooth Low Energy (BLE), ANT, and ZigBee, etc.

The processor 136, according to instructions stored in memory 138, operates a user interface 137 to display physiological information about a patient (or a fetus) so that a clinician can view details/aspects of the patient's physiological condition from the user interface 137. The displayed physiological information may be calculated by the processor 136 based on the digital physiological data received from the sensor device 110. For example, if the sensor device 110 is an ECG monitor, the processor 136 may process the ECG data received from the sensor device 110 to calculate a heart rate, and display the heart rate on the user interface 137. In some embodiments where the sensor device 110 transmits a heart rate to the host device 130, the processor 136 may simply operate to display the heart rate on the user interface 137.

Besides physiological information, the user interface 137 may display various types of information such as but not limited to, the charge level of the battery 132, the sensor device 110 connected to the host device 130, malfunction of the sensor device 110 or the host device 130, and so on.

The battery 132 supplies power to the magnetic detection unit 131 (described in more detail below), transceiver 135, processor 136, and user interface 137. Furthermore, when the sensor device 110 is connected to the host device 130, power is further distributed from the battery 132 to the sensor device 110 via the interface 120. The battery 132 may be any battery capable of providing sufficient power and in some embodiments, includes a rechargeable battery. In some embodiments, the host device 130 includes a voltage regulator (not shown in FIG. 1) connected to the battery 132 and configured to regulate the power distribution within the host device 130 and to the sensor device 110.

It should be understood that the host device 130 as shown in FIG. 1 is for illustration not for limitation. Any suitable host device 130 may be used, which may have more, fewer, and/or different components than what are shown in FIG. 1.

The interface 120 is comprised of a first connector 122 at the side of the sensor device 110 and a second connector 124 at the side of the host device 130. The interface 120 can transfer power from the host device 130 to the sensor device 110 and data (e.g., physiological data) between the sensor device 110 and the host device 130. In some embodiments, the host device side connector 124 is configured to connect with the connector 122 of various types of sensor devices. For example, the connector 122 may be configured identically for various types of sensor devices. Alternatively, the connector 122 may be configured differently for various types of sensor devices. For example, the connector 122 may have more or fewer connection points for transferring digital physiological data and power depending on the type of sensor device 110 and how many data channels are collected. Although one connector 122 is shown on the sensor device side and one connector 124 is shown on the host device side, it should be understood that multiple connectors can be used at one or both sides. For example, separate connectors can be used for power transfer and data transfer.

In some embodiments, the interface 120 includes three pairs of connection points where two pairs are used for transferring power (e.g., one pair are power terminals and one pair are ground terminals) and one pair are for transferring data. It should be understood that the interface 120 may include any suitable number of connection points.

In some embodiments, the connector 122 (or 124) may be inserted into or otherwise physically connected with the connector 124 (or 122) so that the sensor device 110 is attached to the host device 130. In some embodiments, the connection between the sensor device 110 and the host device 130 does not require physical contact, for example, when the devices are connected via an optical data transfer and a capacitive power transfer or other wireless data and/or power transfer mechanisms.

Host device 130 includes a magnetic detection unit 131 that is configured to determine when sensor device 110 is connected to host device 130 (e.g., when first connector 122 is inserted into, brought into contact with, or otherwise connected to second connector 124). Magnetic detection unit 131 includes a magnetic field generator 133 and one or more magnetic field detectors 134. The magnetic field generator 133 may include a DC coil that generates a magnetic field when power is supplied to the coil, or other suitable magnetic field generator that generates a low energy magnetic field. The magnetic field generated by generator 133 may be a slowly alternating magnetic field, which may improve the signal to noise ratio of the corresponding magnetic field detection relative to a static magnetic field. For example, processor 136 (according to instructions stored on memory 138) or another control unit (such as a control unit included as part of magnetic detection unit 131) may modulate a power supply to the coil of generator 133 in order to selectively generate a magnetic field. For example, generator 133 may be controlled to generate a magnetic field at a specified frequency (e.g., 1 Hz), pulse width, and/or magnitude. The one or more magnetic field detectors 134 may include Hall effect sensors or other magnetic field detectors. The one or more detectors 134 may be configured to send signal(s) to processor 136 indicative of a measured magnetic field.

Sensor device 110 includes a magnetizable part 123 disposed on or embedded in the sensor device 110. For example, the magnetizable part 123 may be included on a surface of first connector 122 or embedded within first connector 122. The magnetizable part 123 may be comprised of a suitable material having magnetic properties (whether spontaneously magnetized in the presence of an external magnetic field, permanently magnetized, or both) and thus can cause a change in the magnetic field generated by generator 133, such as sintered ferrite, nickel, steel, iron, etc. In some embodiments, the magnetizable part includes material where at least some amount of spontaneous magnetization will occur during the detection process (e.g., when the magnetizable part is brought into proximity of the magnetic field generator). The magnetic signature of the target may include some permanent (e.g. remanence) magnetism without departing from the scope of this disclosure, and that permanent magnetism may augment the information detected through the detectors, as explained below. In some examples, first connector 122 itself may act as the magnetizable part. For example, first connector 122 may include a magnetizable coating. However, in some examples first connector 122 may have a body comprised of non-conductive material to ensure electrical safety and biocompatibility. In such examples, the magnetizable part may be provided on or within first connector 122 and may be comprised of a different material than first connector 122.

Thus, the generator 133 may be controlled to generate a magnetic field at a given frequency, such as once per second. The one or more detectors 134 may detect the generated magnetic field and send a signal to the processor 136 indicative of the magnetic field. When the sensor device 110 is not connected to the host device 130, the magnetic field generated by the generator 133 and detected by the detector(s) 134 may be a baseline magnetic field that indicates a sensor device is not connected. Once the sensor device 110 is connected to the host device 130, the magnetizable part 123 is brought into close proximity (e.g., within 1-10 mm) of the magnetic detection unit 131, which causes a change in the magnetic field generated by the generator 133. The change in the magnetic field is detected by the detector(s) 134 and the signal(s) from the detector(s) are sent to the processor 136. Based on the detected change in the magnetic field, the processor 136 (according to instructions stored in memory 138) may determine that the sensor device 110 has been connected to the host device 130 and establish a power/communication connection with the sensor device 110. The power/communication connection may facilitate the transfer of power from the host device 130 to the sensor device 110 and/or the transfer of information (e.g., raw or processed data output from the sensor(s) 115 sent from the sensor device 110 to the host device 130) between the sensor device 110 and the host device 130.

In some examples, in addition to detecting that the sensor device 110 has been connected to the host device 130 based on the change in the magnetic field, the host device 130 may be configured to detect additional information about the sensor device 110 based on the change in magnetic field. For example, if the magnetic field changes by a first, smaller amount, the host device 130 may determine that a first sensor device has been connected. If the magnetic field changes by a second, larger amount, the host device 130 may determine that a second sensor device, different than the first sensor device, has been connected. For example, the first sensor device may be a respiration rate sensor device and the second sensor device may be an SpO2 sensor device. The host device 130 may store information in memory 138 that associates a given change in the magnetic field with a given sensor device type. For example, memory 138 may store a look-up table that indexes change in magnetic field to sensor device type.

In other examples, rather than just relying on the magnitude of the change in the magnetic field (which may lack sufficient detail to convey more information than just two or three different sensor types), the host device 130 may be configured to detect additional information about the sensor device 110 based on the change in magnetic field as detected by two or more detectors 134. For example, the magnetic detection unit 131 may include two, three, four, or more detectors 134, each spaced apart from each other in a predefined manner (e.g., along a linear axis, or arranged into an array). The magnetizable part 123 may be configured (e.g., shaped) such that it causes different changes to the respective magnetic fields detected by each detector. For example, a first segment of the magnetizable part that is proximate to a first detector may cause a first change in the magnetic field detected by the first detector while a second segment of the magnetizable part that is proximate to a second detector may cause a second change in the magnetic field detected by the second detector, where the first and second changes are different. In this way, various information may be communicated to the host device 130, such as sensor device type, sensor device manufacturer, etc. Additional details regarding the magnetic signature imparted by the magnetizable part will be provided below.

In some examples, as explained above, the sensor(s) 115 are configured to be removably attached to the sensor device 110. Thus, the sensor device 110 may include a magnetic detection unit 105 configured to detect when a sensor 115 has been connected to the sensor device 110. The magnetic detection unit 105 may be similar to the magnetic detection unit 131 on the host device 130, and thus may include a magnetic field generator 107 and one or more magnetic field detectors 109. Once the sensor device 110 is connected to the host device 130 (and thus receives power from the host device 130), power may be supplied to the generator 107, thereby causing the generator 107 to generate a magnetic field that is detected by the one or more detectors 109. When a sensor 115 is connected (e.g., when connector 112 is brought into contact or close proximity to connector 119), a magnetizable part 111 on or embedded within connector 112 may cause a change in the magnetic field that is detected by the one or more detectors 109. Based on the change in magnetic field, the sensor device 110 may determine that a sensor 115 has been connected and establish a power/communication connection with the sensor 115. Further, based on the change in magnetic field as detected by the one or more detectors 109, the sensor device 110 may determine the sensor type, sensor manufacturer, sensor orientation, and/or other information.

In examples where the sensor 115 is permanently attached to the sensor device 110, the magnetic detection unit 105 may be dispensed with. Further, while one sensor and associated connector interface is shown in FIG. 1, it is to be understood that more than sensor may connect to the sensor device 110. In such examples, a magnetic field detection unit may be positioned at each connection interface, to allow detection of each sensor when that sensor is connected to the sensor device.

Figure 2A:
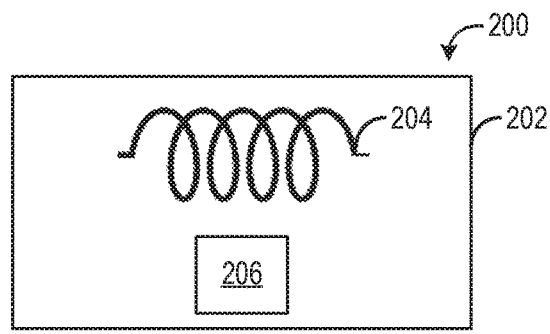
FIG. 2A shows an example of a magnetic detection unit.

FIG. 2A shows an example configuration 200 of a magnetic detection unit 202. Magnetic detection unit 202 may be a non-limiting example of magnetic detection unit 131 and/or magnetic detection unit 105 of FIG. 1 and thus may be included in a host device (such as host device 130) configured to connect to a sensor device (such as sensor device 110) or included in the sensor device, which is configured to connect to a sensor (such as sensor 115). Magnetic detection unit 202 includes a magnetic field generator 204, herein depicted as a DC coil. The generator 204 may be configured to generate a magnetic field when supplied with current (e.g., from a power supply such as a battery). When the supply of current ceases, the generator may not generate a magnetic field. Magnetic detection unit 202 further includes a magnetic field detector 206. The detector 206 may be a Hall effect sensor, inductive sensor, or other sensor configured to detect a magnetic field and output a signal (e.g., a voltage signal) that corresponds to the magnitude of the measured magnetic field. The detector 206 is positioned proximate the generator 204 (e.g., within 1-20 mm of the center of the coil, depending on the configuration of the detector, generator, and device in which the detector and generator are housed); however, in other examples the detector may be positioned further from the generator or in a different location relative to the generator.

Figure 2B:
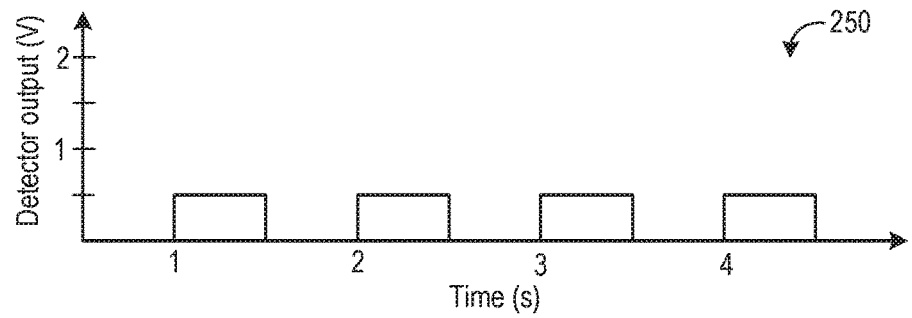
FIG. 2B shows an example graph of a signal output from a detector of the magnetic detection unit of FIG. 2A.

FIG. 2B shows an example graph 250 illustrating the output from the detector 206 (in volts) as a function of time (in seconds). The generator 204 may be supplied current at a frequency of 1 Hz, resulting in one magnetic field pulse per second. The magnetic field may be generated with a pulse width of 0.5 seconds. The detector outputs a signal having a magnitude of 0.5 V for each magnetic field pulse. Thus, with the detector 206 in the illustrated position relative to the generator 204, the baseline magnetic field generated by the generator 206 results in a detector signal having a magnitude of 0.5 V.

Figure 3A:
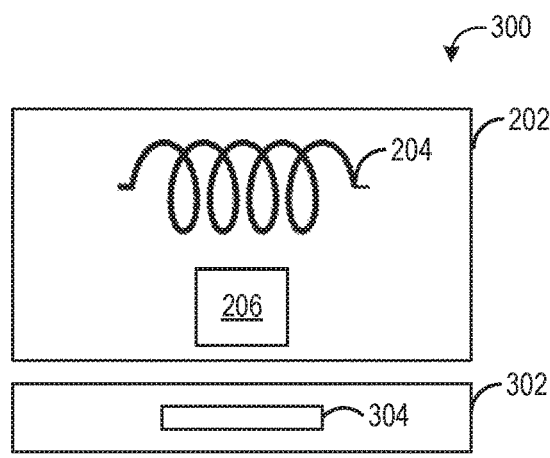
FIG. 3A shows an example of the magnetic detection unit of FIG. 2A in proximity to a first connector and a first magnetizable part.

FIG. 3A shows an example configuration 300 of the magnetic detection unit 202 in proximity to an associated component that includes a connector 302. For example, the connector 302 may be a connector of a sensor device (when the magnetic detection unit 202 is housed in a host device) or a sensor (when the magnetic detection unit 202 is housed in a sensor device), as explained above with respect to FIG. 2A. When the connector 302 is used to connect the sensor device to the host device (or when the connector 302 is used to connect the sensor to the sensor device), a magnetizable part 304 (similar to the magnetizable part 123 and/or magnetizable part 111 of FIG. 1) is brought into proximity of the magnetic field generated by generator 204 (e.g., within 1-20 mm). The presence of the magnetizable part 304 may change the magnetic field sensed by the detector 206. The magnetizable part 304 may be comprised of any material or particles that have magnetic properties. In the configuration 300 of FIG. 3A, the magnetizable part 304 may a uniform piece of material (e.g., steel) that has a consistent thickness, density, etc., across an entirety of the part.

Figure 3B:
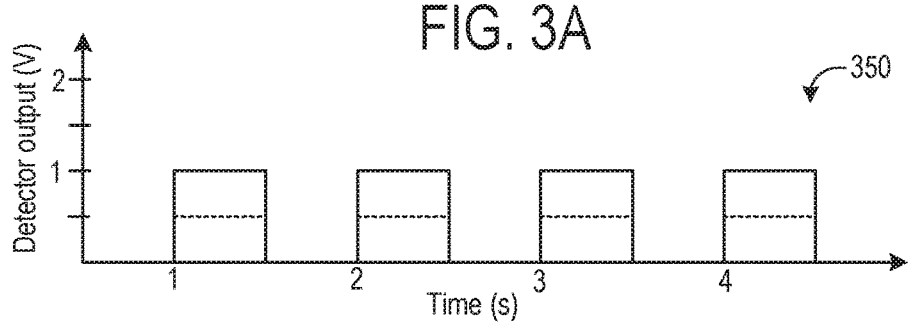
FIG. 3B shows an example graph of a signal output from the detector of the magnetic detection unit when in proximity of the first connector and the first magnetizable part of FIG. 3A.

FIG. 3B shows an example graph 350 illustrating the output from the detector 206 (in volts) as a function of time (in seconds) when the magnetizable part 304 is close enough to change the magnetic field sensed by the detector 206. As described above, the generator 204 may be supplied current at a frequency of 1 Hz, resulting in one magnetic field pulse per second. The magnetic field may be generated with a pulse width of 0.5 seconds. Due to the presence of the magnetizable part 304, the detector outputs a signal having a magnitude of 1 V for each magnetic field pulse. Thus, with the detector 206 in the illustrated position relative to the generator 204 and with the magnetizable part 304 having the uniform shape and material properties as described above, the magnetic field detected by the detector 206 results in a detector signal (e.g., a magnitude of 1 V) that is different (e.g., larger magnitude) than the baseline magnetic field generated by the generator (shown in dotted lines in FIG. 3B).

Figure 3C:
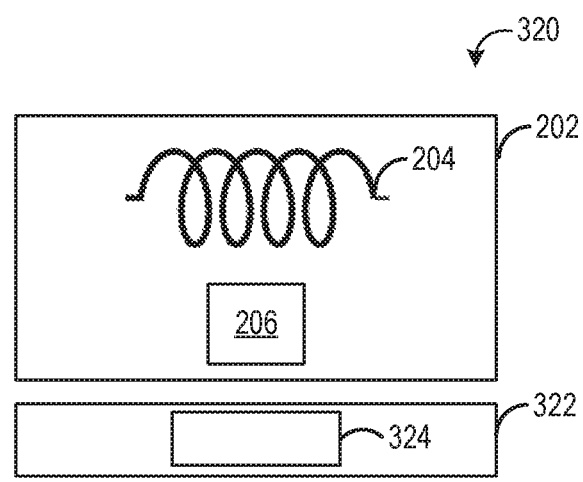
FIG. 3C shows an example of the magnetic detection unit of FIG. 2A in proximity to a second connector and a second magnetizable part.
Figure 3D:
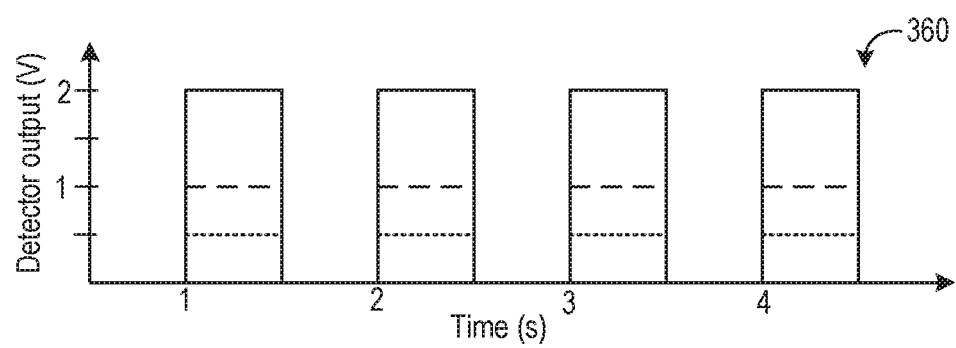
FIG. 3D shows an example graph of a signal output from the detector of the magnetic detection unit when in proximity of the second connector and second magnetizable part of FIG. 3C.

As one example, a host device that houses the magnetic detector unit 202 may be configured to identify that a sensor device has been connected to the host device when the voltage signal output by the detector matches the voltage signal shown in FIG. 3B (e.g., the detector outputs a signal with a higher voltage magnitude than the baseline signal shown in FIG. 2B). In some examples, the thickness of the magnetizable part on the connector may be different in different sensor devices. Thus, the host device may determine that a first sensor device (including magnetizable part 304) has been connected when the voltage signal output by the detector matches the voltage signal shown in FIG. 3B (e.g., having a magnitude of 1 V), but the host device may determine that a second, different sensor device has been connected when the voltage signal output by the detector has a different magnitude (such as 2 V, due to the magnetizable part on the second sensor device having a greater thickness than the magnetizable part 304). As shown in the configuration 320 of FIG. 3C, a second connector 322 that is included as part of a second sensor device or second sensor may be brought into proximity of the magnetic detection unit 202 (e.g., when the connector is inserted in or otherwise connected to the host device or sensor device). The second connector 322 includes a second magnetizable part 324 that is thicker than the magnetizable part 304 of FIG. 3A. As a result, and as shown in graph 360 of FIG. 3D, the voltage signal output by the detector 206 has a larger magnitude (2 V) than the magnitude of the baseline signal (0.5 V, shown by the dotted line) and the magnitude of the signal produced when the magnetizable part 304 is present (1 V, shown by the dashed line).

In this way, the host device (or sensor device) may determine that a sensor device (or sensor) has been connected when the detected magnetic field changes relative to the baseline magnetic field (e.g., increases by at least a first threshold amount, such as increases by more than 10% of the baseline magnetic field). The host device or sensor device may identify that a first component (e.g., first sensor device or first sensor) has been connected when the magnetic field changes by more than the first threshold amount but changes by less than a second threshold amount. The host device or sensor device may identify that a second component (e.g., second sensor device or second sensor) has been connected when the magnetic field changes by more than the first threshold amount and more than the second threshold amount. By doing so, not only can the host device or sensor device detect that a component has been connected, but the host device or sensor device may also detect what type of sensor device or sensor has been connected. Other information may be conveyed in a similar manner. For example, rather than detect sensor type, the change in magnetic field may be used to confirm that the sensor device or sensor was manufactured by an original or accepted manufacturer.

Figure 4A:
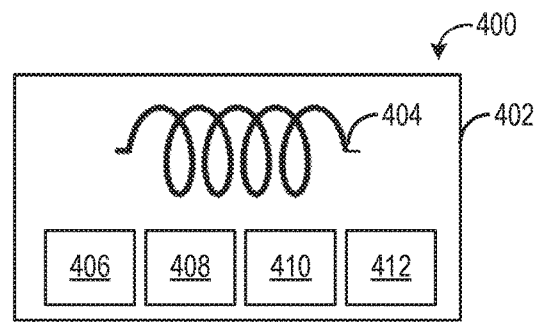
FIG. 4A shows another example of a magnetic detection unit.

FIG. 4A shows an example configuration 400 of a magnetic detection unit 402. Magnetic detection unit 402 may be a non-limiting example of magnetic detection unit 131 and/or magnetic detection unit 105 of FIG. 1 and thus may be included in a host device (such as host device 130) configured to connect to a sensor device (such as sensor device 110) or included in the sensor device, which is configured to connect to a sensor (such as sensor 115). Magnetic detection unit 402 includes a magnetic field generator 404, herein depicted as a DC coil. The generator 404 may be configured to generate a magnetic field when supplied with current (e.g., from a power supply such as a battery). When the supply of current ceases, the generator may not generate a magnetic field. Magnetic detection unit 402 further includes four magnetic field detectors (detector 406, detector 408, detector 410, and detector 412) arranged linearly along an axis. The detectors may be Hall effect sensors, inductive sensors, or other sensors configured to detect a magnetic field and output a signal (e.g., a voltage signal) that corresponds to the magnitude of the measured magnetic field. Two of the detectors are positioned proximate the center of the generator 404 (e.g., detectors 408 and 410 are positioned within 1-5 mm of the center of the coil) and two of the detectors are located along respective edges of the generator (e.g., detector 406 is positioned at a first end of the coil and detector 412 is positioned at a second end of the coil). However, in other examples, the detectors may be positioned further from the generator or in different positions relative to the generator.

Figure 4B:
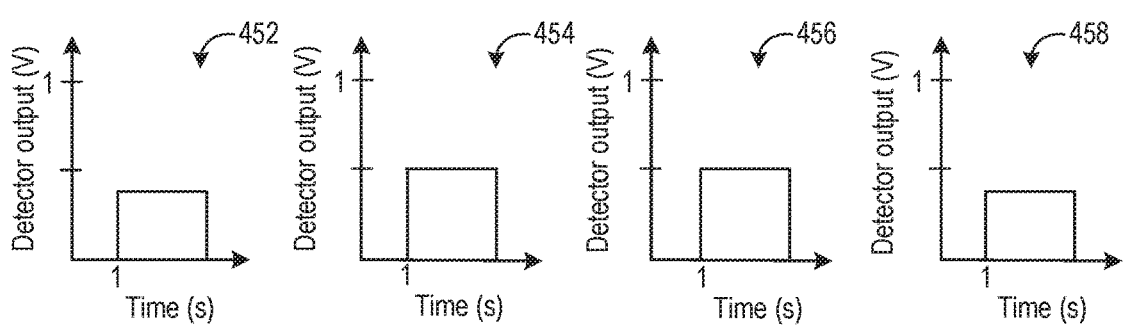
FIG. 4B shows an example graph of a signal output from the detectors of the magnetic detection unit of FIG. 4A.

FIG. 4B shows an example set of graphs 450 illustrating the output from each detector (in volts) as a function of time (in seconds). The generator 404 may be supplied current at a frequency of 1 Hz, resulting in one magnetic field pulse per second. The magnetic field may be generated with a pulse width of 0.5 seconds. Similar to detector 206, detectors 408 and 410 each output a signal having a magnitude of 0.5 V for each magnetic field pulse, as shown by graph 454 and graph 456, respectively. (It will be appreciated that only one pulse is shown for each graph.) However, detector 406 and detector 412 each output a voltage signal having a slightly lower magnitude, as shown by graph 452 and graph 458, respectively. Herein, the voltage output by detectors 406 and 412 is shown as having a magnitude of approximately 0.4 V, due to detectors 406 and 412 being located at the respective edges of the coil, where the magnetic field generated by the generator 404 is lower. By including more than one detector, the magnetic detector unit 402 may be configured to detect a spatially varying magnetic field resulting from the non-uniform magnetic field generated by the generator 404.

Figure 5A:
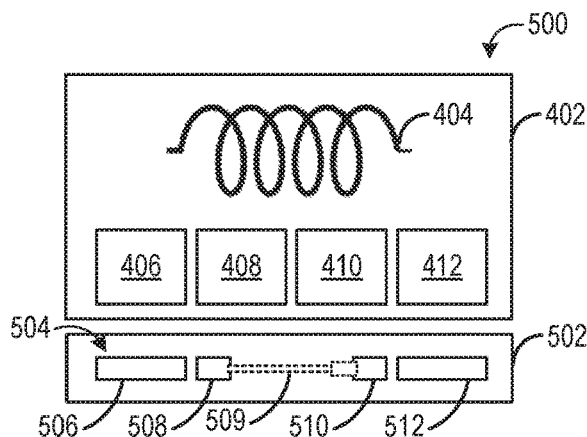
FIG. 5A shows an example of the magnetic detection unit of FIG. 4A in proximity to a first connector and a first magnetizable part.

FIG. 5A shows an example configuration 500 of the magnetic detection unit 402 in proximity to an associated component that includes a connector 502. For example, the connector 502 may be a connector of a sensor device or a sensor, as explained above with respect to FIG. 2A. When the connector 502 is used to connect the sensor device to the host device (or when the connector 502 is used to connect the sensor to the sensor device), a magnetizable part 504 (similar to the magnetizable part 123 and/or magnetizable part 111 of FIG. 1) is brought into proximity of the magnetic field generated by generator 404. The presence of the magnetizable part 504 may change the magnetic field sensed by the detectors 406, 408, 410, and 412. The magnetizable part 504 may be comprised of any metal material or particles that have magnetic properties.

In the configuration 500 of FIG. 5A, the magnetizable part 504 is comprised of multiple segments of material, including a first segment 506 configured to be positioned proximate the detector 406, a second segment 508 configured to be positioned proximate the detector 408, a third segment 510 configured to be positioned proximate the detector 410, and a fourth segment 512 configured to be positioned proximate the detector 412. The first segment 506 and the fourth segment 512 may be of the same dimensions, e.g., the same thickness and length, and the second segment 508 and third segment 510 may of the same dimensions (e.g., same thickness and length). The first segment 506 and fourth segment 512 may be longer than the second segment 508 and the third segment 510, thus resulting in the second segment 508 and the third segment 510 having less magnetizable material than the first segment 506 and the fourth segment 512. As a result, the signals output from the four detectors may be different, due to the spatially varying magnetic field that results from the differing properties of the segments of the magnetizable part. Further, at least in some examples, the magnetizable part 504 includes a bridge 509. The bridge may span the second segment 508 and the third segment 510, and may be comprised of a magnetizable material that has magnetic properties but that is more brittle than the other segments of the magnetizable part 504. For example, the bridge 509 may be comprised of ferrite while the other segments of the magnetizable part 504 may be comprised of a magnetizable metal such as steel. Additionally, in the illustrated example, the bridge 509 may be asymmetric, such that the portion of the bridge that is close to/contacts the third segment 510 is thicker than the portion that contacts or is close to the second segment 508.

In this way, each segment may "encode" a different piece of information. For example, sensor type (e.g., respiration rate, SpO2, ECG, and so forth) may be determined based on the properties of the first segment (e.g., the thickness of the first segment). Sensor device manufacturer or sensor manufacturer may be determined based on the properties (e.g., thickness) of the fourth segment. Sensor device state or sensor state (such as degradation state and/or orientation) may be determined based on the properties of the second segment, third segment, and bridge.

Figure 5B:
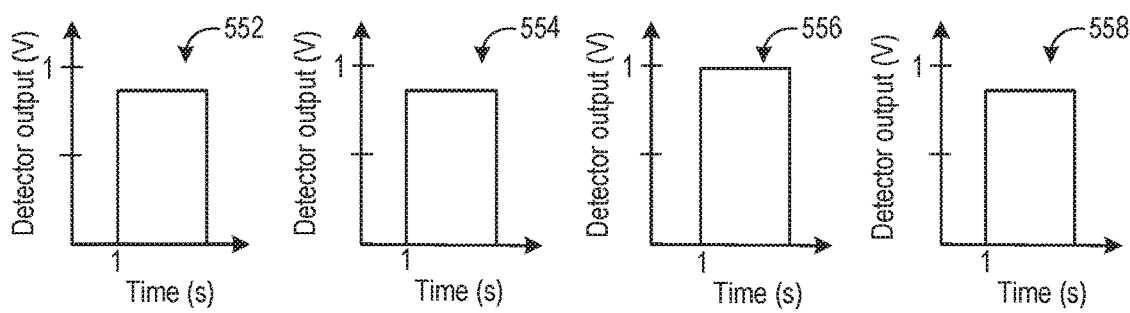
FIG. 5B shows an example set of graphs of the signals output from the detectors of the magnetic detection unit when in proximity of the first connector and the first magnetizable part of FIG. 5A.

FIG. 5B shows an example set of graphs 550 illustrating the output from each detector (in volts) as a function of time (in seconds). The generator 404 may be supplied current at a frequency of 1 Hz, resulting in one magnetic field pulse per second. The magnetic field may be generated with a pulse width of 0.5 seconds. Due to the presence of the magnetizable part 504, detector 406, detector 408, and detector 412 each output a signal having a higher magnitude than the respective baseline signals (e.g., a magnitude of 0.75 V) for each magnetic field pulse, as shown by graph 552, graph 554, and graph 558, respectively. (It will be appreciated that only one pulse is shown for each graph.) However, detector 410 outputs a voltage signal with an even higher magnitude (e.g., 1 V) due to the detector 410 being closer to the generator than the outer detectors and also due to the bridge 509 having a greater thickness at the third segment, as shown by graph 556.

As one example, when the connector 502 is positioned near the magnetic detection unit 402, the host device or sensor device housing the magnetic detection unit may be configured to determine the sensor device type or sensor type based on the magnitude of the signal output by the detector 406. The host device or sensor device may be configured to determine the sensor device manufacturer or sensor manufacturer based on the magnitude of the signal output by the detector 412. The host device or sensor device may be configured to determine whether the sensor device or sensor is degraded, and also determine the sensor device or sensor orientation based on the magnitudes of the signals output by the detector 408 and the detector 410. For example, if the orientation of the sensor device or sensor were flipped relative to that shown in FIG. 5A, the magnitude of the signal output by the detector 408 may be higher than the magnitude of the signal output by the detector 410.

Figure 5C:
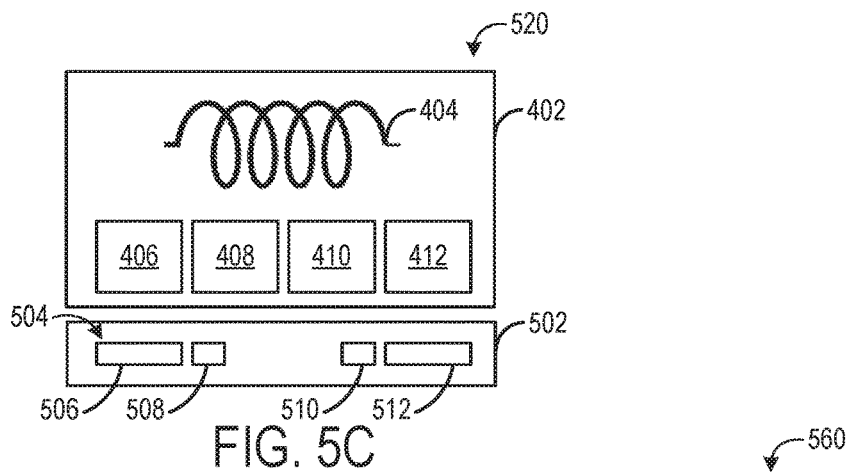
FIG. 5C shows an example of the magnetic detection unit of FIG. 4A in proximity to the first connector and the first magnetizable part when the first magnetizable part is degraded.
Figure 5D:
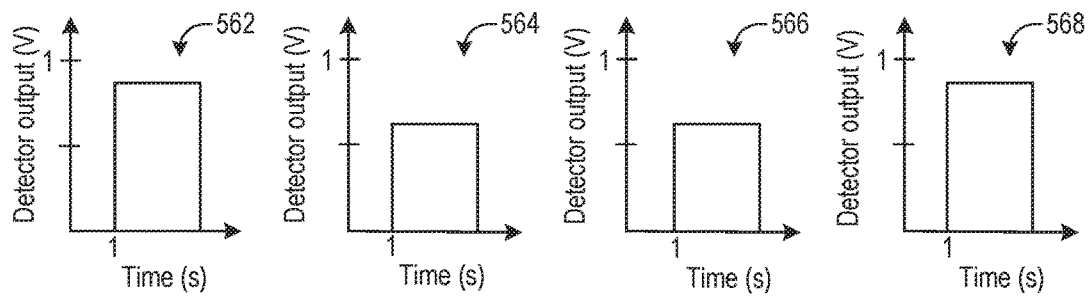
FIG. 5D shows an example set of graphs of the signals output from the detector of the magnetic detection unit when in proximity of the first connector and first magnetizable part of FIG. 5C.

FIGS. 5C and 5D illustrate an example configuration 520 where the bridge 509 has degraded (e.g., broken apart) and is no longer present on the magnetizable part 504. As mentioned above, the bridge 509 may be frangible, and thus may degrade (e.g., break apart) when exposed to certain conditions, such as high temperature, low temperature, excessive pressure or torque, or other conditions that may cause degradation of the sensor device or sensor. In this way, the bridge 509 may be act as a proxy for potential degradation to the sensor device or sensor itself. For example, if the sensor device or sensor is exposed to extreme heat or pressure, components of the sensor device or sensor may degrade, thereby compromising performance of the sensor device or sensor. The bridge 509 may likewise degrade under these conditions, which may be detected by the host device (or sensor device) based on the output from the detectors, as shown in FIG. 5D.

FIG. 5D shows an example set of graphs 560 illustrating the output from each detector (in volts) as a function of time (in seconds) for the configuration 520 of FIG. 5C. The generator 404 may be supplied current at a frequency of 1 Hz, resulting in one magnetic field pulse per second. The magnetic field may be generated with a pulse width of 0.5 seconds. Due to the presence of the magnetizable part 504, detector 406 and detector 412 each output a signal having a higher magnitude than the respective baseline signals (e.g., a magnitude of 0.75 V) for each magnetic field pulse, as shown by graph 562 and graph 568, respectively. (It will be appreciated that only one pulse is shown for each graph.) Due to the bridge 509 degrading and no longer being present, detector 408 and detector 410 each output a signal having a magnitude that reflects the change in magnetic field due to the second segment 508 and third segment 510, respectively, and thus the signals output by the detector 408 and the detector 410 have lower magnitudes than the respective signals output when the bridge 509 was present. Due to the smaller material in the second and third segments relative to the first and fourth segments, the magnitudes of the signals output by the detector 408 and the detector 410 are smaller (e.g., 0.6 V, as shown by graphs 564 and 566, respectively) than the magnitudes of the signals output by the detectors 406 and 412.

Figure 6A:
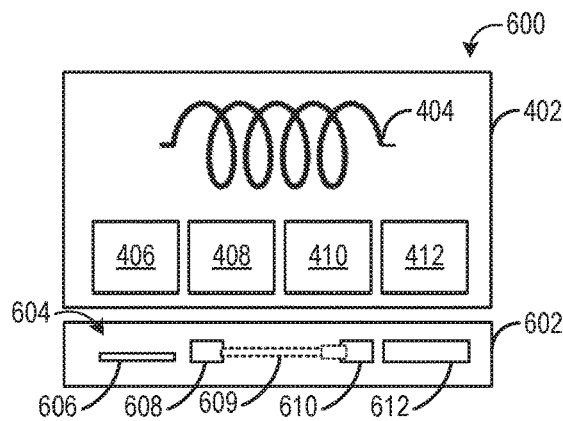
FIG. 6A shows an example of the magnetic detection unit of FIG. 4A in proximity to a second connector and a second magnetizable part.
Figure 6B:
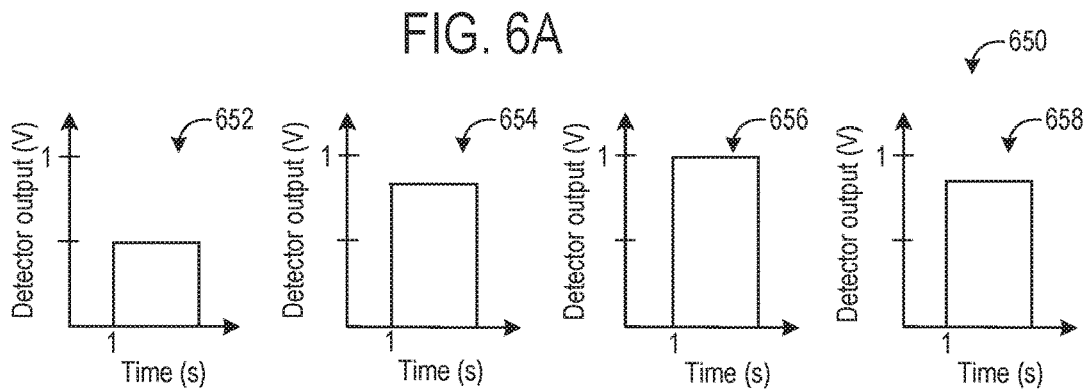
FIG. 6B shows an example set of graphs of the signals output from the detectors of the magnetic detection unit when in proximity of the second connector and the second magnetizable part of FIG. 6A.

As another example, as shown in FIGS. 6A-6B, one or more of the segments of the magnetizable part may be varied to convey to the host device (or sensor device) additional information regarding properties of the sensor device (or sensor). FIG. 6A shows an example configuration 600 of the magnetic detection unit 402 in proximity to an associated component that includes a connector 602. For example, the connector 602 may be a connector of a sensor device or a sensor, as explained above with respect to FIG. 2A. When the connector 602 is used to connect the sensor device to the host device (or when the connector 602 is used to connect the sensor to the sensor device), a magnetizable part 604 (similar to the magnetizable part 123 and/or magnetizable part 111 of FIG. 1) is brought into proximity of the magnetic field generated by generator 404. The presence of the magnetizable part 604 may change the magnetic field sensed by the detectors 406, 408, 410, and 412 relative to the baseline (e.g., when no magnetizable part is present). The magnetizable part 604 may be similar to the magnetizable part 504 and thus includes a first segment 606, a second segment 608, a third segment 610, a fourth segment 612, and a bridge 609. Each segment may be virtually identical to the corresponding segment of the magnetizable part 504, other than the first segment 606, which is thinner than the first segment 506. As a result, as shown by a set of graphs 650 of FIG. 6B, the signals output by each of detectors 408, 410, and 412 (shown by graphs 654, 656, and 658, respectively) may be similar to the signals illustrated by graphs 554, 556, and 558 of FIG. 5B. However, the signal output by the detector 406 while in the configuration 600 (shown by graph 652) has a magnitude (e.g., 0.5 V) that is smaller than the magnitude of the signal shown in graph 552 of FIG. 5B. Based on the magnitude of the signal output by detector 406, the host device (or sensor device) may identify that connector 602 and magnetizable part 604 are part of a second component (e.g., a second sensor device or a second sensor) that is different than the first component that includes connector 502 and magnetizable part 504.

As one example, a host device that houses the magnetic detector unit 402 may be configured to identify that a sensor device has been connected to the host device when the voltage signals output by the detectors match the voltages shown in FIG. 5B, 5D, or 6B (e.g., at least one detector outputs a signal with a higher voltage than the respective baseline signal shown in FIG. 4B). The host device may be configured to identify that the sensor device is a first sensor device (e.g., a respiration rate sensor device) when the voltage signals output by one or more of the detectors match a magnetic signature associated with the first sensor device, such as when the voltage signal output by the detector 406 matches the signals shown in graph 552 of FIG. 5B or graph 562 of FIG. 5D. The host device may be configured to identify that the sensor device is a second sensor device (e.g., an SpO2 sensor device) when the voltage signals output by one or more of the detectors match a magnetic signature associated with the second sensor device, such as when the voltage signal output by the detector 406 matches the signal shown in graph 652 of FIG. 6B. Further, the host device may be configured to determine that no sensor device is connected to the host device when each detector outputs a baseline voltage signal that has a magnitude that corresponds to the magnetic field generated by the generator, such as the signals shown in FIG. 4B. Further still, the host device may be configured to determine that the connected sensor device is functional (e.g., not degraded) when the signals output from one or more of the detectors match a magnetic signature associated with a functional sensor device (e.g., when the signals output from the detectors 408 and 410 match the signals shown in graphs 554 and 556 of FIG. 5B and graphs 654 and 656 of FIG. 6B) or determine that the connected sensor device is not functional (e.g., degraded) when the signals output from one or more of the detectors match a magnetic signature associated with a nonfunctional sensor device (e.g., when the signals output from the detectors 408 and 410 match the signals shown in graphs 564 and 566 of FIG. 5D). Additionally, the host device may be configured to determine an orientation of the sensor device (when more than one orientation is possible) based on the signals output from one or more of the detectors matching a magnetic signature associated with a first orientation or a second orientation.

Likewise, a sensor device that houses a magnetic detection unit, such as the magnetic detection unit 202 or 402, may be configured to determine that no sensor is connected to the sensor device when the signal output by the detector(s) matches a baseline signal (e.g., has a magnitude that corresponds to the magnetic field generated by the generator of the magnetic detection unit). The sensor device may be configured to determine that a sensor is connected to the sensor device when the signal output by the detector(s) changes relative to the baseline signal by an expected amount (e.g., has a magnitude that is within a threshold range of a magnitude that corresponds to an expected change in the magnetic field generated by the generator of the magnetic detection unit, due to the presence of a magnetizable part on the connector of the sensor). Further, the sensor device may be configured to identify the type of sensor, manufacturer of the sensor, and/or other information based on a magnetic signature of the magnetizable part, e.g., the magnitude of the signal, spatial variation of the magnetic field, etc. As one example, the sensor device may be configured to identify that a first sensor (e.g., a respiration rate electrode patch) has been connected when the signal from the detector 406 matches the signal illustrated in graph 552 of FIG. 5B and identify that a second sensor (e.g., a pulse oximeter) has been connected when the signal from the detector 406 matches the signal illustrated in graph 652 of FIG. 6B.

It is to be understood that the above-described magnetizable parts, detector arrangement, and magnetic signature-additional information associations are exemplary in nature and that other configurations are possible. For example, when multiple detectors are present, the detectors may be arranged in an array (e.g., a two by two array), the detectors may surround the generator, the detectors may not be aligned along a common axis, etc. As another example, the magnetizable part may not be comprised of multiple separate segments as shown in FIGS. 5A, 5C, and 6A, but may instead be comprised of a single piece of material. Further, rather than have varying material thickness to differentially change the magnetic field, the different segments may be located at different positions relative to the generator.

Thus, regardless of the exact configuration of the detectors, generator, and magnetizable part, the generator may generate a magnetic field that may be modified by the magnetizable part when the magnetizable part is brought into proximity of the magnetic field. The detectors may sense the change in the magnetic field and the output from the detectors may be used by a processor of a suitable device (the host device or sensor device) to determine that an associated component housing the magnetizable part has been connected to the device, and in some examples, determine some additional information about the associated component (such as sensor type or manufacturer). Further, by including a magnetizable part that can change the magnetic field in a spatially varying manner, even further information may be conveyed to the device (such as the orientation of the associated component, functionality of the associated component, sensor type and/or manufacturer, etc.).

Figure 7:
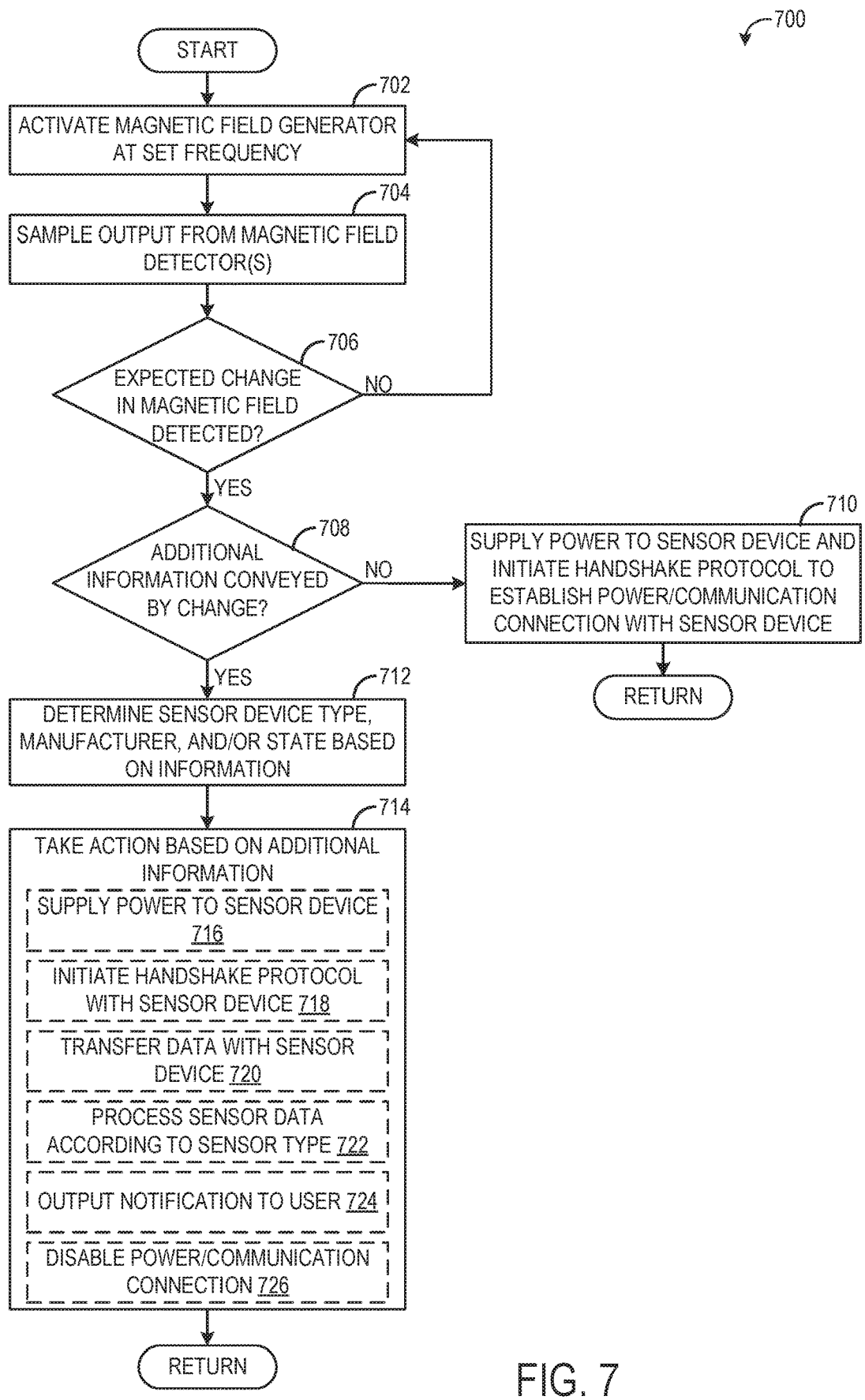
FIG. 7 is a flow chart illustrating a method for detecting, which a host device, that a sensor device has been connected to the host device.

FIG. 7 is a flow chart illustrating a method 700 for detecting that a sensor device has been connected to a host device. Method 700 may be executed by a host device (e.g., host device 130 of FIG. 1) according to instructions stored in memory (e.g., memory 138) of the host device, where the instructions are executable by a processor of the host device (e.g., processor 136). The host device includes a magnetic detection unit (e.g., magnetic detection unit 131 including a magnetic field generator (e.g., generator 133) and one or more magnetic field detectors (e.g., detectors 134) configured to detect the presence of a corresponding magnetizable part on the sensor device (e.g., magnetizable part 123).

At 702, the magnetic field generator is activated at a set frequency. When activated, the magnetic field generator generates a magnetic field in the localized vicinity of the generator and the detector(s). To activate the generator, the host device (e.g., via the processor executing instructions stored in memory) may control a supply of current to the generator. For example, the host device may supply current to the generator according to a predetermined frequency, pulse width, and amplitude to cause the generator to periodically generate a magnetic field of a predetermined level. The magnetic field may be generated at a suitable frequency, such as 1 Hz or 10 Hz.

At 704, the output from the magnetic field detector(s) is sampled. The magnetic field detector(s) is configured to generate a signal (e.g., a voltage signal) that corresponds to the level of the magnetic field (e.g., as the magnetic field increases, the magnitude of the voltage signal may also increase). At 706, method 700 includes determining if an expected change in the magnetic field is detected. As explained previously, the magnetic field generator may generate a magnetic field having a predetermined or known level, resulting in a baseline signal output by the detector(s). The signal output by the detector(s) may change relative to the baseline when a magnetizable part of a sensor device is brought into proximity of the host device (such as when the connector 122 is mechanically connected with the connector 124, which brings the magnetizable part 123 into the magnetic field of the generator 133). The host device may determine that the magnetic field has changed by the expected amount when one or more parameters of the signal output by the detector(s) changes by an expected amount, such as the amplitude of the signal increasing by an amount greater than a threshold. If the expected change in the magnetic field is not detected, for example if the magnetic field does not change relative to the baseline, method 700 loops back to 702 to continue to activate the magnetic field and sample the output from the magnetic field detector(s). Because the magnitude of the magnetic field has not changed, the host device may assume that a sensor device has not been connected, and thus the host device may continue to periodically generate the magnetic field and look for the change in the magnetic field. In the meantime, the host device may not supply power to a sensor device or communicate with a sensor device.

If the expected change in the magnetic field is detected, the host device determines that a sensor device is connected (e.g., physically connected) to the host device due to the presence of the magnetizable part of the sensor device, which changes the magnetic field. However, additional information may also be conveyed by the magnetizable part that may be identified based on the output of the detector(s). Thus, at 708, method 700 includes determining if additional information is conveyed by the change in magnetic field (e.g., based on the output of the detector(s)). The host device may determine that the additional information is being conveyed if the output of the detector(s) matches output that the host device associates with information other than the presence of a sensor device.

In some examples, the host device may not be configured to detect if additional information is being conveyed by the magnetizable part. For example, the host device may only be configured to determine whether the magnetic field measured by the magnetic field generators has changed by a threshold amount, indicating that a sensor device has been connected. In such examples, and/or when the magnetizable part does not convey any additional information (e.g., when the magnetizable part does not change the magnetic field in a manner that the host device associates with any additional information), method 700 proceeds to 710 to supply power to the sensor device and initiate a handshake protocol to establish a power/communication connection with the sensor device. In some embodiments, in order to mitigate the risk of misuse or other rare events resulting in a high DC offset without the sensor device actually being attached (e.g., if something other than sensor device triggers a change in the magnetic field that is detected by the detectors), the host device may initiate a secondary handshake process before fully establishing the power/communication connection with the sensor device. In particular, the host device may send a request for acknowledgement to the sensor device via the interface established when the sensor device is connected to the host device. In response to the request, the sensor device sends an acknowledgement message to the host device. In response to receiving the acknowledgement message, the host device determines that the sensor device is present and establishes the connection with sensor device. Data may be transferred between the host device and sensor device upon the power/communication connection being established. In some examples, power may be supplied to the sensor device before the handshake protocol commences, as the sensor device may not store sufficient power to respond to the handshake request without receiving power from the host device. In other examples, power may be supplied from the host device only after the handshake protocol has completed and the host device confirms the sensor device is connected. The power/communication connection may be fully wireless (e.g., both data and power may be transferred/supplied wirelessly), fully wired (e.g., both data and power may be transferred/supplied via a wired connection), or partially wireless (e.g., one of the data and power may be transferred/supplied via a wireless connection while the other may be transferred/supplied via a wired connection). Upon establishing the power/communication connection with the sensor device, method 700 returns.

If the host device determines that additional information is conveyed in the change in magnetic field (e.g., based on the signal output by the detector(s)), method 700 proceeds to 712 to determine the sensor device type, sensor device manufacturer, sensor device state, and/or other information based on the additional information. The sensor device type may include the physiological parameter that the sensor device is configured to monitor, such as respiration rate, SpO2, blood pressure, etc. The sensor device manufacturer may be an approved manufacturer (such that accurate patient monitoring and device functioning is provided) or a non-approved manufacturer (such that accurate patient monitoring and device functioning is not necessarily provided). The sensor device state may include sensor device degradation state (e.g., functional versus degraded), sensor device orientation, or other information about the sensor device.

As explained above, the host device may determine that additional information is being conveyed by the magnetizable part when the output from the detector(s) of the magnetic detection unit matches one or more predetermined magnetic signatures. The host device may store in memory a look-up table or other data structure that indexes sensor device type, sensor device manufacturer, sensor device state, and/or additional information by magnetic signature. The magnetic signatures may each include one or more voltage thresholds, where each voltage threshold is specific to a signal output from a specific magnetic field detector.

For example, referring to FIGS. 5A-6B, a first magnetic signature may include a magnitude of a first signal output from a first detector being within a range around a first threshold (e.g., within 0.1 V of 0.8 V) and a second magnetic signature may include a magnitude of the first signal output from the first detector being within a range around a second threshold (e.g., within 0.1 V of 1 V). When the host device receives the signals output from the detectors, the host device may determine the magnetic signature(s) from the detector output and may enter the magnetic signature(s) in the look-up table to determine what additional information is being conveyed. The host device may determine hat, for example, the first magnetic signature indicates that a first sensor device (e.g., a respiration rate sensor device) having a first magnetizable part (e.g., the magnetizable part 504) is connected to the host device or that the second magnetic signature indicates that a second sensor device (e.g., an SpO2 sensor device) having a second magnetizable part (e.g., the magnetizable part 604) is connected to the host device. A third magnetic signature may include a magnitude of a second signal output from a second detector being within a range around a third threshold (e.g., within 0.1 V of 0.8 V), such as when the signal output from the detector 412 of FIG. 5A or FIG. 6A is at 0.8 V. When the host device determines that the magnetizable part causes the third magnetic signature, the host device may identify that the connected sensor device was manufactured by an approved (e.g., original) manufacturer. When the host device determines that the magnetizable part does not cause the third magnetic signature, the host device may identify that the connected sensor device was manufactured by a non-approved manufacturer. A fourth magnetic signature may include a magnitude of a third signal output from a third detector and a magnitude of a fourth signal output from a fourth detector each being greater than a fourth threshold (e.g., 0.8 V or greater), such as when the signals output from the detectors 408 and 410 of FIG. 5A or FIG. 6A are at 0.8 V or greater. The fourth magnetic signature may indicate that the sensor device state is a functional state, for example.

At 714, an action is taken based on the additional information determined from the change in magnetic field resulting from the proximity of the magnetizable part. The action taken may depend on the additional information. As a first example, taking an action may include supplying power to the sensor device, as indicated at 716. When the host device confirms that a sensor device is connected to the host device, due to the change in the magnetic field, the host device may start to supply power to the sensor device (e.g., via a wired or wireless power connection), so that a handshake protocol may be initiated with the sensor device, as indicated at 718, and, if the proper sensor device is confirmed via the handshake protocol, a power/communication connection may be established, as indicated at 720. The communication connection may include a wired connection (e.g., direct signal level communication) or a wireless connection. However, as explained above, in some examples the power may not be supplied until the handshake protocol is complete. Once the power/communication connection has been established, taking an action may include processing sensor data according to the sensor type, as indicated at 722. For example, if the sensor type is determined at 712, the data obtained by the sensor device that is sent to the host device may be processed in an appropriate manner for that sensor device. For example, the data may be processed differently depending on the type of sensor (e.g., respiration rate versus SpO2). Further, in some examples, if the sensor device type is identified at 712, the sensor device type may be displayed via the user interface of the host device, at the patient monitoring hub, and/or the processing system.

As another example, taking an action may include outputting a notification to a user, as indicated at 724. For example, if the sensor device type or the sensor device manufacturer is not expected (e.g., the sensor device was not manufactured by an approved manufacturer or the sensor device is a type not expected for the medical facility, such as a sensor device configured for an adult patient being used in a pediatric or neonatal unit), or if the sensor device is degraded, a notification may output (e.g., to a user interface such as a display screen) to inform a user. For example, if one of the detected magnetic signatures indicates that the sensor device is potentially degraded, a user of the host device may be notified by outputting a notification via a user interface of the host device, patient monitoring system, or processing system (e.g., by displaying the notification of a display screen of the host device, patient monitoring system, or processing system). In this way, the user may opt to test the sensor device before commencing patient monitoring, or the user may opt to replace the sensor device with a sensor device that is confirmed to be functional. As another example, if the sensor device manufacturer is not expected (e.g., if the magnetic signature associated with an approved manufacturer is not detected), the user may be notified via a notification from the user interface that the sensor device is not an approved sensor device, which may allow the user to switch to an approved sensor device. In some examples, if the sensor device type or manufacturer is not expected, or if degradation of the sensor device is suspected, the sensor device type, manufacturer, and/or degradation state may be confirmed by reevaluating the change in magnetic field induced by the magnetizable part of the sensor device, e.g., the user may disconnect and then reconnect the sensor device.

As another example, taking an action may include disabling the power/communication connection between the host device and sensor device if the sensor device manufacturer is not expected (e.g., the sensor device is not an approved sensor device) or if the sensor device is degraded, as indicated at 726. In this way, the risk of inaccurate patient monitoring (e.g., by a non-approved sensor device or by a degraded sensor device) may be reduced by preventing the host device from being connected to the non-approved or degraded sensor device. Disabling the power/communication connection may include ceasing the supply of power to the sensor device, which may disable most or all functions of the sensor device (including data transfer). When the power/communication connection is disabled, a mechanical connection between the host device and sensor device may still be present (e.g., until a user manually disconnects the host device and sensor device).

Thus, method 700 of FIG. 7 allows a host device to determine when a sensor device has been connected to the host device based on a change in a magnetic field at the host device caused by the sensor device. In particular, the sensor device may include a magnetizable part that causes a predefined change in the magnetic field at the host device. The host device may detect the change in the magnetic field and then initiate a connection with the sensor device, whereby power may be supplied to the sensor device. Further, in some examples, the magnetizable part may be configured to change the magnetic field in such a manner (e.g., in a spatially varying manner) that the host device may detect additional information about the sensor device, such as the type of sensor device, manufacturer of the sensor device, state of the sensor device, etc. The host device may then take one or more appropriate actions depending on the additional information. If the additional information indicates that the sensor device is not made by an approved manufacturer or that the sensor device is degraded, the power and/or data connection between the host device and sensor device may be severed to ensure accurate patient monitoring, for example. If the host device determines that the sensor device is functional, approved, and/or of the appropriate type, the power/communication connection may be established. In this way, confirmation of the connection of the appropriate sensor device may be confirmed in a low-cost, low-power manner that does not require a physical connection between the host device and sensor device.

Further, the magnetic detection described herein does not require a physical connection between parts of the host device and parts of the sensor device. Rather, while the connectors of the devices may physically connect to enable the power and/or data transfer (and to save on packaging space for the final sensor system when the sensor system is used to monitor a patient), the magnetic detection itself does not require a physical connection, only that the devices be brought into close proximity. This may provide increased flexibility when wireless connections are desired. Additionally, the magnetic detection described herein only requires power to be supplied to one side of the system (e.g., to the magnetic field generator) while the other side (e.g., the magnetizable part) is configured to impart information while unpowered. In this respect, the magnetic detection is different than other communication protocols such as BLUETOOTH®. Further, the magnetic detection described herein relies on relatively low magnetic fields, in contrast to other magnetic sensors. As such, the strong magnets required in conventional magnetic sensors may be dispensed with, which may reduce or avoid potential contamination of the components of the sensor system with debris attracted to the strong magnets.

Figure 8:
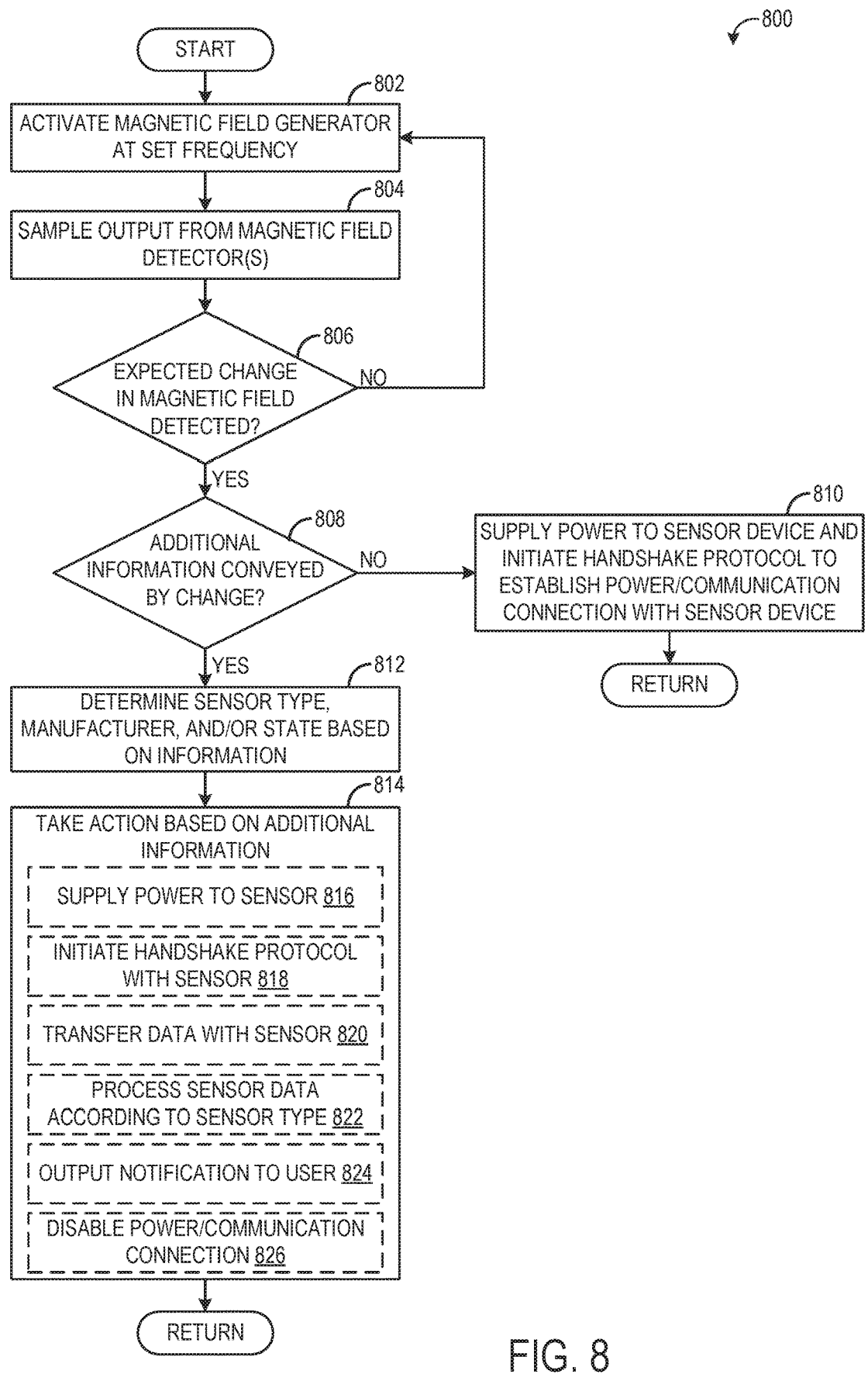
FIG. 8 is a flow chart illustrating a method for detecting, with a sensor device, that a sensor has been connected to the sensor device.

FIG. 8 is a flow chart illustrating a method 800 for detecting that a sensor or other accessory has been connected to a sensor device. Method 800 may be executed by a sensor device (e.g., sensor device 110 of FIG. 1) according to instructions stored in memory (e.g., memory 118) of the sensor device, where the instructions are executable by a processor of the sensor device (e.g., processor 117). The sensor device includes a magnetic detection unit (e.g., magnetic detection unit 105) including a magnetic field generator (e.g., generator 107) and one or more magnetic field detectors (e.g., detectors 109) configured to detect the presence of a corresponding magnetizable part on the sensor or accessory (e.g., magnetizable part 111 on a connector 112 of sensor 115).

At 802, the magnetic field generator is activated at a set frequency. When activated, the magnetic field generator generates a magnetic field in the localized vicinity of the generator and the detector(s). To activate the generator, the sensor device (e.g., via the processor executing instructions stored in memory) may control a supply of current to the generator. For example, the sensor device may supply current to the generator according to a predetermined frequency, pulse width, and amplitude to cause the generator to periodically generate a magnetic field of a predetermined level. The magnetic field may be generated at a suitable frequency, such as 1 Hz or 10 Hz. Because the sensor device may lack a battery or other energy storage device, the generator may only be activated once the sensor device is connected to the host device, as explained above with respect to FIG. 7.

At 804, the output from the magnetic field detector(s) is sampled. The magnetic field detector(s) is configured to generate a signal (e.g., a voltage signal) that corresponds to the level of the magnetic field (e.g., as the magnetic field increases, the magnitude of the voltage signal may also increase). At 806, method 800 includes determining if an expected change in the magnetic field is detected. As explained previously, the magnetic field generator may generate a magnetic field having a predetermined or known level, resulting in a baseline signal output by the detector(s). The signal output by the detector(s) may change relative to the baseline when a metallic/magnetizable part of a sensor is brought into proximity of the host device (such as when the connector 112 is connected with the connector 119, which brings the magnetizable part 111 into the magnetic field of the generator 107). The sensor device may determine that the magnetic field has changed by the expected amount when one or more parameters of the signal output by the detector(s) changes by an expected amount, such as the amplitude of the signal increasing by an amount greater than a threshold. If the expected change in the magnetic field is not detected, for example if the magnetic field does not change relative to the baseline, method 800 loops back to 802 to continue to activate the magnetic field and sample the output from the magnetic field detector(s). When the magnetic field does not change, the sensor device may assume that no sensor is connected, and thus no power supply or data transfer may occur.

If the expected change in the magnetic field is detected, the sensor device determines that a sensor (or other accessory) is connected to the sensor device (e.g., mechanically connected) due to the presence of the magnetizable part of the sensor, which changes the magnetic field at the sensor device. However, additional information may also be conveyed by the magnetizable part that may be identified based on the output of the detector(s). Thus, at 808, method 800 includes determining if additional information is conveyed by the change in magnetic field (e.g., based on the output of the detector(s)). The sensor device may determine that the additional information is being conveyed if the output of the detector(s) matches output that the sensor device associates with information other than the presence of a sensor.

In some examples, the sensor device may not be configured to detect if additional information is being conveyed by the magnetizable part. For example, the sensor device may only be configured to determine whether the magnetic field measured by the magnetic field generators has changed by a threshold amount, indicating that a sensor has been connected. In such examples, and/or when the magnetizable part does not convey any additional information (e.g., when the magnetizable part does not change the magnetic field in a manner that the sensor device associates with any additional information), method 800 proceeds to 810 to supply power to the sensor and initiate a handshake protocol to establish a power/communication connection with the sensor. In some embodiments, in order to mitigate the risk of misuse or other rare events resulting in a high DC offset without the sensor actually being attached (e.g., if something other than the sensor triggers a change in the magnetic field that is detected by the detectors), the sensor device may initiate a secondary handshake process before fully establishing the power/communication connection with the sensor. In particular, the sensor device may send a request for acknowledgement to the sensor via the interface established when the sensor is connected to the sensor device. In response to the request, the sensor sends an acknowledgement message to the sensor device. In response to receiving the acknowledgement message, the sensor device determines that the sensor is present and establishes the connection with sensor. Data may be transferred between the sensor device and sensor upon the power/communication connection being established. In some examples, power may be supplied to the sensor before the handshake protocol commences, as the sensor may not store sufficient power to respond to the handshake request without receiving power from the sensor device. In other examples, power may be supplied from the sensor device only after the handshake protocol has completed and the host device confirms the sensor is connected. The power/communication connection may be fully wireless (e.g., both data and power may be transferred/supplied wirelessly), fully wired (e.g., both data and power may be transferred/supplied via a wired connection), or partially wireless (e.g., one of the data and power may be transferred/supplied via a wireless connection while the other may be transferred/supplied via a wired connection). Upon establishing the power/communication connection with the sensor, method 800 returns.

If the sensor device determines that additional information is conveyed in the change in magnetic field (e.g., based on the signal output by the detector(s)), method 800 proceeds to 812 to determine the sensor type, sensor manufacturer, sensor state, and/or other information based on the additional information. The sensor type may include the physiological parameter that the sensor is configured to monitor, such as respiration rate, SpO2, blood pressure, etc. The sensor manufacturer may be an approved manufacturer (such that accurate patient monitoring and device functioning is provided) or a non-approved manufacturer (such that accurate patient monitoring and device functioning is not necessarily provided). The sensor state may include sensor degradation state (e.g., functional versus degraded), sensor orientation, or other information about the sensor, such as intended patient use (e.g., whether the sensor is configured to monitor an adult or a pediatric patient).

As explained above, the sensor device may determine that additional information is being conveyed by the magnetizable part of the sensor when the output from the detector(s) of the magnetic detection unit matches one or more predetermined magnetic signatures. The sensor device may store in memory a look-up table or other data structure that indexes sensor type, sensor manufacturer, sensor state, and/or additional information by magnetic signature. The magnetic signatures may each include one or more voltage thresholds, where each voltage threshold is specific to a signal output from a specific detector.

For example, referring to FIGS. 5A-6B, a first magnetic signature may include a magnitude of a first signal output from a first detector being within a range around a first threshold (e.g., within 0.1 V of 0.8 V) and a second magnetic signature may include a magnitude of the first signal output from the first detector being within a range around a second threshold (e.g., within 0.1 V of 1 V). When the sensor device receives the signals output from the detectors, the sensor device may determine the magnetic signature(s) from the detector output and may enter the magnetic signature(s) in the look-up table to determine what additional information is being conveyed. The sensor device may determine hat, for example, the first magnetic signature indicates that a first sensor (e.g., a respiration rate sensor) having a first magnetizable part (e.g., the magnetizable part 504) is connected to the sensor device or that the second magnetic signature indicates that a second sensor (e.g., a pulse oximeter) having a second magnetizable part (e.g., the magnetizable part 604) is connected to the sensor device. A third magnetic signature may include a magnitude of a second signal output from a second detector being within a range around a third threshold (e.g., within 0.1 V of 0.8 V), such as when the signal output from the detector 412 of FIG. 5A or FIG. 6A is at 0.8 V. When the sensor device determines that the magnetizable part causes the third magnetic signature, the sensor device may identify that the connected sensor was manufactured by an approved (e.g., original) manufacturer. When the sensor device determines that the magnetizable part does not cause the third magnetic signature, the sensor device may identify that the connected sensor was manufactured by a non-approved manufacturer. A fourth magnetic signature may include a magnitude of a third signal output from a third detector and a magnitude of a fourth signal output from a fourth detector each being greater than a fourth threshold (e.g., 0.8 V or greater), such as when the signals output from the detectors 408 and 410 of FIG. 5A or FIG. 6A are at 0.8 V or greater. The fourth magnetic signature may indicate that the sensor state is a functional state, for example.

At 814, an action is taken based on the additional information determined from the change in magnetic field resulting from the proximity of the magnetizable part. The action taken may depend on the additional information. As a first example, taking an action may include supplying power to the sensor device, as indicated at 816. When the sensor device confirms that a sensor is connected to the sensor device, due to the change in the magnetic field, the sensor device may start to supply power to the sensor, so that a handshake protocol may be initiated with the sensor as indicated at 818, and, if the proper sensor is confirmed via the handshake protocol, a power/communication connection may be established, as indicated at 820. However, as explained above, in some examples the power may not be supplied until the handshake protocol is complete. The power connection may be wired or wireless. Likewise, the data connection may be wired or wireless. Further, in some examples, the sensor may not be configured to receive power, and thus only a data connection may be established (e.g., when the sensor includes ECG electrodes).

Once the power/communication connection has been established, taking an action may include processing sensor data according to the sensor type, as indicated at 822. For example, if the sensor type is determined at 812, the data obtained by the sensor that is sent to the sensor device may be processed in an appropriate manner for that sensor. For example, the data may be processed differently depending on the type of sensor (e.g., respiration rate versus SpO2). Further, in some examples, if the sensor type is identified at 812, the sensor type may be displayed via the user interface of the host device, at the patient monitoring hub, and/or the processing system.

As another example, taking an action may include outputting a notification to a user, as indicated at 824. For example, if the sensor type or the sensor manufacturer is not expected (e.g., the sensor was not manufactured by an approved manufacturer, the sensor device is configured to receive and process data received from a pulse oximeter, but a respiration rate sensor electrode system is connected instead, or the sensor is a type not expected for the medical facility, such as a sensor configured for an adult patient being used in a pediatric or neonatal unit), or if the sensor is degraded, a notification may output (e.g., to a user interface such as a display screen) to inform a user. For example, if one of the detected magnetic signatures indicates that the sensor is potentially degraded, a user may be notified by outputting a notification via a user interface of the host device, patient monitoring system, or processing system (e.g., by displaying the notification of a display screen of the host device, patient monitoring system, or processing system). In this way, the user may opt to test the sensor before commencing patient monitoring, or the user may opt to replace the sensor with a sensor that is confirmed to be functional. As another example, if the sensor manufacturer is not expected (e.g., if the magnetic signature associated with an approved manufacturer is not detected), the user may be notified via a notification from the user interface that the sensor is not an approved sensor, which may allow the user to switch to an approved sensor. In some examples, if the sensor type or manufacturer is not expected, or if degradation of the sensor is suspected, the sensor type, manufacturer, and/or degradation state may be confirmed by reevaluating the change in magnetic field induced by the magnetizable part of the sensor, e.g., the user may disconnect and then reconnect the sensor.

As another example, taking an action may include disabling the power/communication connection between the sensor device and sensor if the sensor manufacturer is not expected (e.g., the sensor is not an approved sensor) or if the sensor is degraded, as indicated at 826. In this way, the risk of inaccurate patient monitoring (e.g., by a non-approved sensor or by a degraded sensor) may be reduced by preventing the sensor device from being connected to the non-approved or degraded sensor. Disabling the power/communication connection may include ceasing the supply of power to the sensor, which may disable most or all functions of the sensor (including data transfer). When the power/communication connection is disabled, a mechanical connection between the sensor device and host device may still be present (e.g., until a user manually disconnects the sensor device and sensor).

Additionally, in some examples, the sensor device may at least partially control aspects of the connected sensor, and the manner in which the sensor device controls the sensor may be adjusted based on the additional information. As one example, if the sensor is a pulse oximeter, the sensor device may control activation of the light emitters (e.g., the LEDs) of the pulse oximeter, such as controlling the pulse width, amplitude, and frequency of the current supplied to the light emitters. Because different patients may have different signal attenuation, the parameters of the light emitters (e.g., pulse width, amplitude, and/or frequency) may be adjusted based on patient parameters, which may be determined by the additional information. For example, the magnetizable part of the pulse oximeter connector may be adapted to convey that the pulse oximeter is sized for a pediatric patient and the sensor device may detect this additional information and control the light emitters accordingly, which may be different than when the pulse oximeter is sized for an adult patient.

Thus, method 800 of FIG. 8 allows a sensor device to determine when a sensor or other accessory has been connected to the sensor device based on a change in a magnetic field at the sensor device caused by the sensor. In particular, the sensor may include a magnetizable part that causes a predefined change in the magnetic field at the sensor device. The sensor device may detect the change in the magnetic field and then initiate a connection with the sensor, whereby power may be supplied to the sensor. Further, in some examples, the magnetizable part may be configured to change the magnetic field in such a manner (e.g., in a spatially varying manner) that the sensor device may detect additional information about the sensor, such as the type of sensor, manufacturer of the sensor, state of the sensor, etc. The sensor device may then take one or more appropriate actions depending on the additional information. If the additional information indicates that the sensor is not made by an approved manufacturer or that the sensor is degraded, the power and/or data connection between the sensor device and sensor may be severed to ensure accurate patient monitoring, for example. If the sensor device determines that the sensor is functional, approved, and/or of the appropriate type, the power/communication connection may be established. In this way, confirmation of the connection of the appropriate sensor may be confirmed in a low-cost, low-power manner that does not require a physical connection between the sensor device and sensor.

Figure 9:
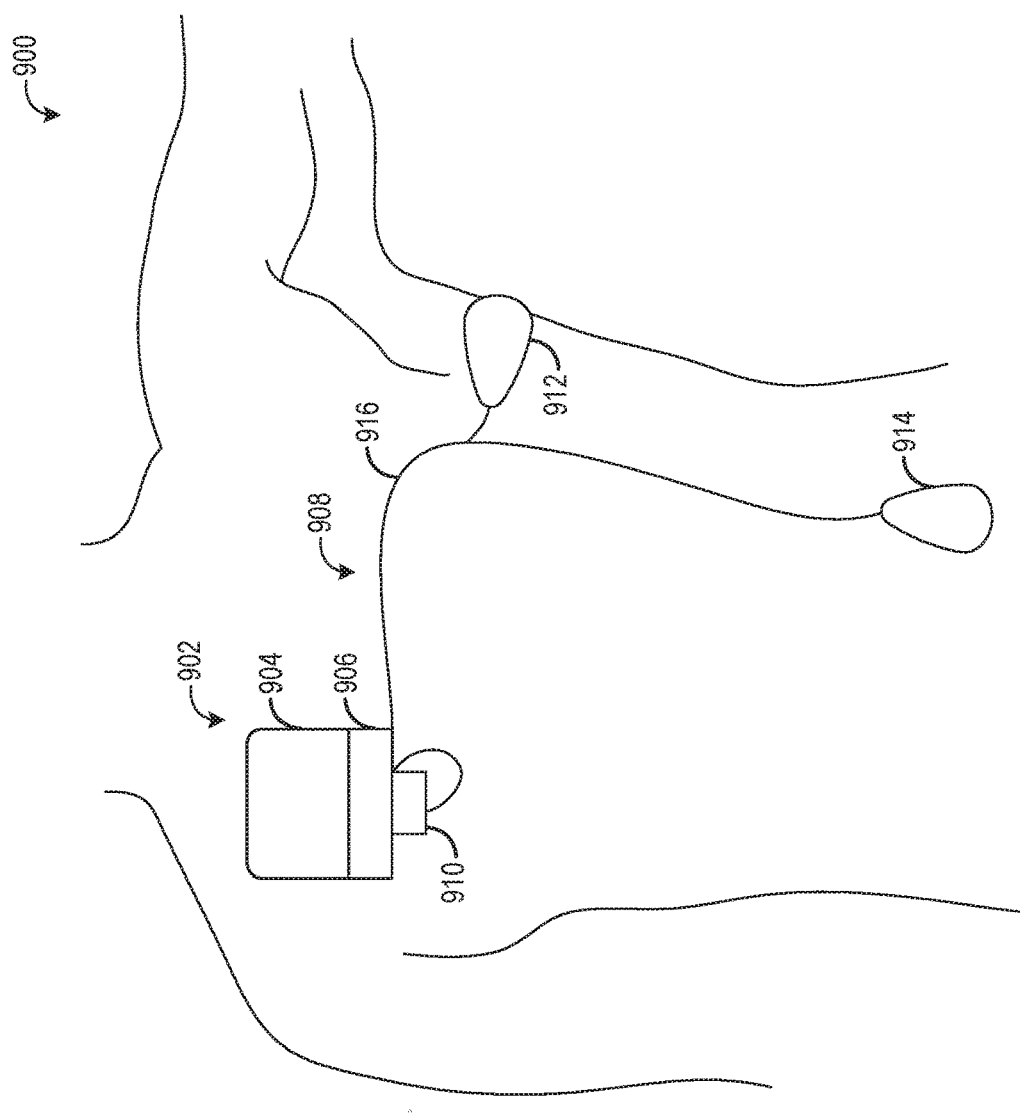
FIG. 9 shows an example patient monitoring system including a sensor system that includes a host device connected to a sensor device and a respiration rate sensor connected to the sensor device.
Figure 9:
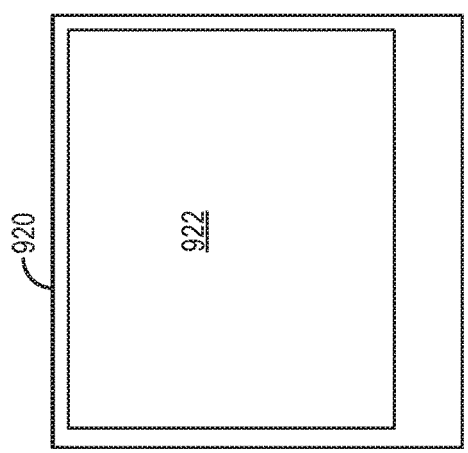

FIG. 9 shows an example patient monitoring system 900 including a sensor system 902. Sensor system 902 is a non-limiting example of sensor system 100 and thus includes a host device 904, a sensor device 906, and a sensor 908. As shown in FIG. 9, the sensor device 906 is mechanically connected to the host device 904 and the sensor 908 is mechanically connected to the sensor device 906.

The sensor system 902 is in the form of a respiration rate monitor, and thus the sensor 908 includes a plurality of electrodes, including electrode 912 and electrode 914, each of which are connected to a sensor base/connector 910 via a cable harness 916 (also referred to as a cable). While not shown in FIG. 9, in some examples, an electrode and/or adhesive patch of the sensor 908 may be positioned behind the host device 904 and/or sensor device 906. The electrodes (and adhesive patch) are shown as being coupled to a chest of a patient.

The host device 904 is configured to communicate wirelessly with a patient monitoring hub 920 and/or a processing system. In some examples, the host device 904 may communicate with the processing system (not shown in FIG. 9) via the patient monitoring hub 920. In other examples, the patient monitoring hub may be dispensed with and the host device 904 may communicate with the processing system directly. The patient monitoring hub 920 may include a display screen 922, via which physiological data collected by sensor 908 may be displayed to a user and/or via which notifications may be displayed to a user.

Figure 10:
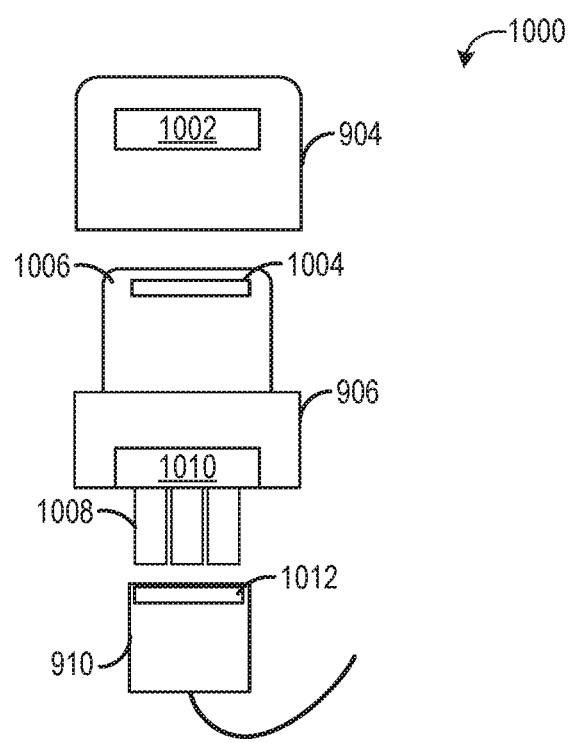
FIG. 10 shows an exploded view of the sensor system of FIG. 9.

FIG. 10 shows a partially exploded view 1000 of the sensor system 902 of FIG. 9. The sensor system 902 includes the host device 904. The host device 904 may include a magnetic detection unit 1002. The magnetic detection unit 1002 may be similar to the magnetic detection unit 131 of FIG. 1, and may include a magnetic field generator and one or more magnetic field detectors. The host device 904 includes a connector that is not fully visible in the view of FIG. 10.

The sensor system 902 includes the sensor device 906. The sensor device 906 includes a connector 1006. The connector 1006 is configured to connect mechanically to the connector of the host device 904. The connector 1006 includes a magnetizable part 1004, which has a form factor that is configured to induce a predefined change in a magnetic field generated at the host device (e.g., by the generator of the magnetic detection unit 1002). When the sensor device 906 is connected to the host device 904, the connector 1006 is positioned within the counterpart connector of the host device 904 and the magnetizable part 1004 is brought into close proximity to the magnetic detection unit 1002. The magnetizable part 1004 thereby induces a change in the magnetic field at the host device that is detected by the one or more detectors of the magnetic detection unit 1002.

The sensor device 906 further includes a connector 1008 configured to connect to the sensor base/connector 910 of the sensor 908. As shown, the connector 1008 includes three prongs. As an example, one of the prongs may be a power prong, configured to supply power to the sensor; one of the prongs may be a ground prong; and one of the prongs may be a data prong configured to transfer data between the sensor device 906 and the sensor. The sensor base/connector 910 may include counterpart prong receivers that are configured to accommodate the prongs and facilitate the power/communication connection between the sensor device and the sensor.

The sensor device 906 includes a magnetic detection unit 1010 positioned proximate the connector 1008. The magnetic detection unit 1010 is similar to the magnetic detection unit 105, and includes a magnetic field generator and one or more magnetic field detectors. The sensor base/connector 910 includes a magnetizable part 1012 that includes a form factor that is configured to induce a predefined change in the magnetic field at the sensor device (e.g., the magnetic field generated by the generator of the magnetic detection unit 1010). When the sensor base/connector 910 is mechanically connected to the sensor device 906 via the connector 1008, the magnetizable part 1012 is brought into close proximity of the magnetic detection unit 1010. The magnetizable part 1012 thereby induces a change in the magnetic field at the sensor device that is detected by the one or more detectors of the magnetic detection unit 1010.

Figure 11:
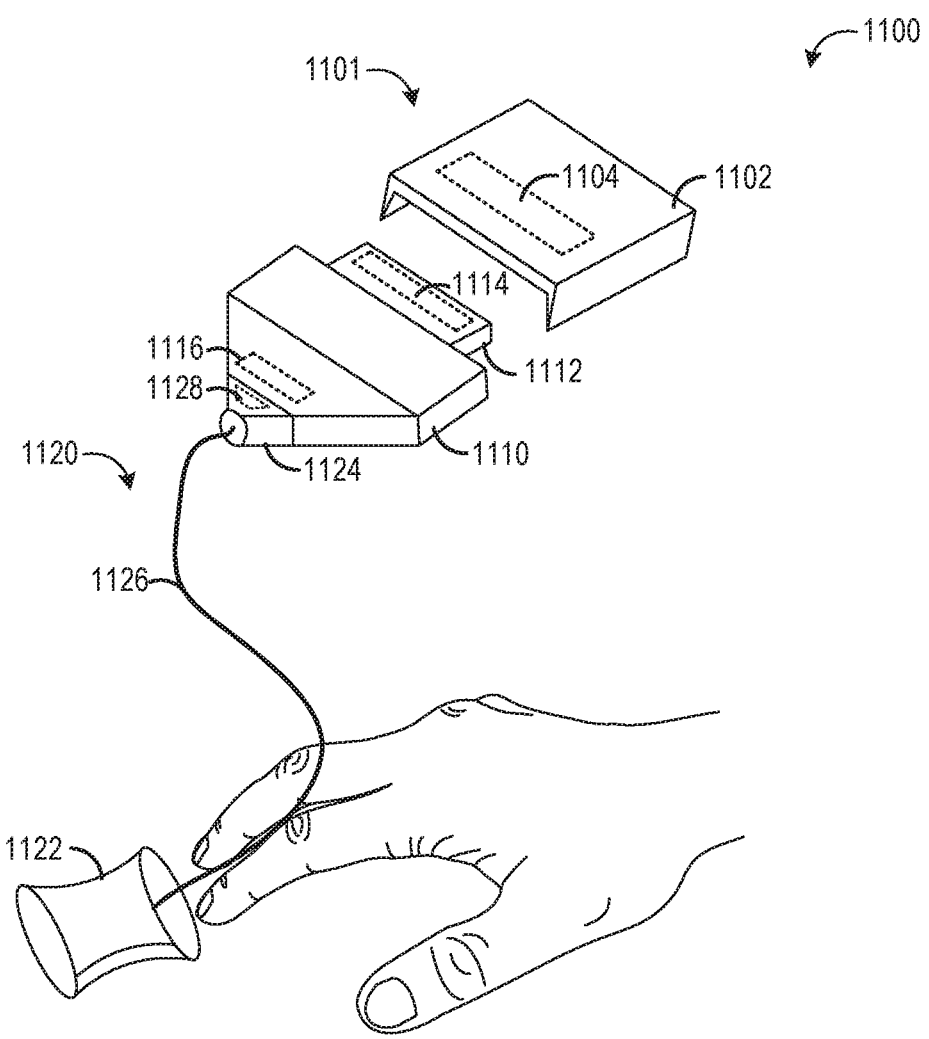
FIG. 11 shows an example patient monitoring system including a sensor system that includes a host device connected to a sensor device and a pulse oximeter connected to the sensor device.

FIG. 11 shows an example patient monitoring system 1100 including a sensor system 1101. Sensor system 1101 is a non-limiting example of sensor system 100 and thus includes a host device 1102, a sensor device 1110, and a sensor 1120. As shown in FIG. 10, the sensor device 1110 is separated from the host device 1102 and the sensor 1120 is mechanically connected to the sensor device 1110.

The sensor system 1101 is in the form of an SpO2 monitor, and thus the sensor 1120 includes a pulse oximeter 1122 coupled to a connector 1124 via a cable 1126. The pulse oximeter 1122 includes one or more light emitters (e.g., light emitting diodes) configured to emit light in one or more wavelengths and one or more detectors to detect the emitted light after the emitted light has passed through patient tissue. In the example shown in FIG. 11, the pulse oximeter 1122 is shaped to fit over a finger of a patient, although other configurations are possible (e.g., the pulse oximeter may be adapted to accommodate a toe of a patient, include a patch configured to be placed over a nose of a patient, etc.). The host device 1102 is configured to communicate wirelessly with a patient monitoring hub and/or a processing system, similar to the host device and patient monitoring hub/processing system communication discussed above with respect to FIG. 9.

The host device 1102 may include a magnetic detection unit 1104. The magnetic detection unit 1104 may be similar to the magnetic detection unit 131 of FIG. 1, and may include a magnetic field generator and one or more magnetic field detectors. The host device 1102 includes a connector that is not fully visible in the view of FIG. 11, although it will be appreciated from FIG. 11 that the host device 1102 is shaped to accommodate the counterpart connector of the sensor device (described below).

The sensor system 1101 includes the sensor device 1110. The sensor device 1110 includes a connector 1112. The connector 1112 is configured to connect mechanically to the connector of the host device 1102. The connector 1112 includes a magnetizable part 1114, which has a form factor that is configured to induce a predefined change in a magnetic field generated at the host device (e.g., by the generator of the magnetic detection unit 1104). When the sensor device 1110 is connected to the host device 1102, the connector 1112 is positioned within the counterpart connector of the host device 1102 and the magnetizable part 1114 is brought into close proximity to the magnetic detection unit 1104. The magnetizable part 1114 thereby induces a change in the magnetic field at the host device that is detected by the one or more detectors of the magnetic detection unit 1104.

The sensor device 1110 further includes a second connector configured to connect to the sensor base/connector 1124 of the sensor 1120. The sensor device 1110 includes a magnetic detection unit 1116 positioned at or proximate the second connector. The magnetic detection unit 1116 is similar to the magnetic detection unit 105 of FIG. 1, and includes a magnetic field generator and one or more magnetic field detectors. The sensor base/connector 1124 includes a magnetizable part 1128 that includes a form factor that is configured to induce a predefined change in the magnetic field at the sensor device (e.g., the magnetic field generated by the generator of the magnetic detection unit 1116). When the sensor base/connector 1124 is mechanically connected to the sensor device 1110, the magnetizable part 1128 is brought into close proximity of the magnetic detection unit 1116. The magnetizable part 1128 thereby induces a change in the magnetic field at the sensor device that is detected by the one or more detectors of the magnetic detection unit 1116.

While FIG. 11 shows a different host device than the host device illustrated in FIGS. 9 and 10, in some examples the sensor device of FIGS. 9 and 10 and the sensor device of FIG. 11 may be configured to connect the same host device. In this way, the host device may be a universal host device that may connect to various different sensor devices.

Figure 12:
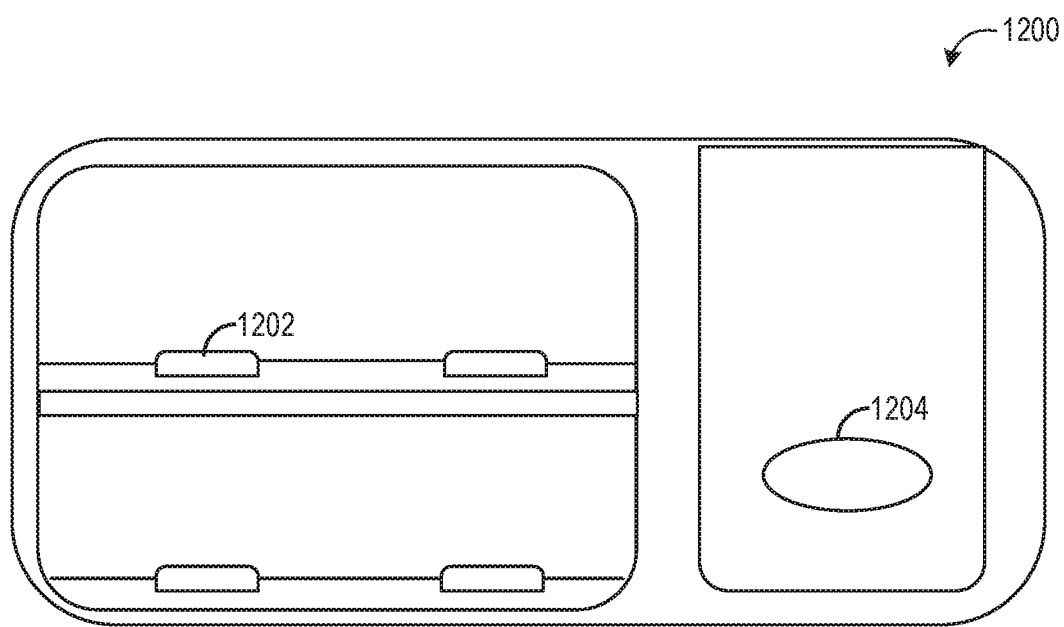
FIG. 12 shows an example charging system.

As explained previously, the host devices described herein may each include a battery that may be rechargeable. Further, in some examples, to facilitate patient and/or care provider mobility, the patient monitoring hub may also include a rechargeable battery. In this way, the sensor systems described herein may enable a patient that is being monitored to have enhanced mobility. FIG. 12 shows a charging station 1200 that is configured to charge one or more host device batteries and a battery of a patient monitoring hub. As shown, charging station 1200 includes a plurality of charging ports each configured to charge a respective host device, such as port 1202. As shown in FIG. 12, charging station 1200 includes four charging ports for charging respective host devices. Further, charging station 1200 includes a charging port 1204 configured to charge a battery of a patient monitoring hub. While not shown in FIG. 12, charging station 1200 includes a power cord that is configured to connect to a main power supply, in order to supply power to the various charging ports.

Figure 13:
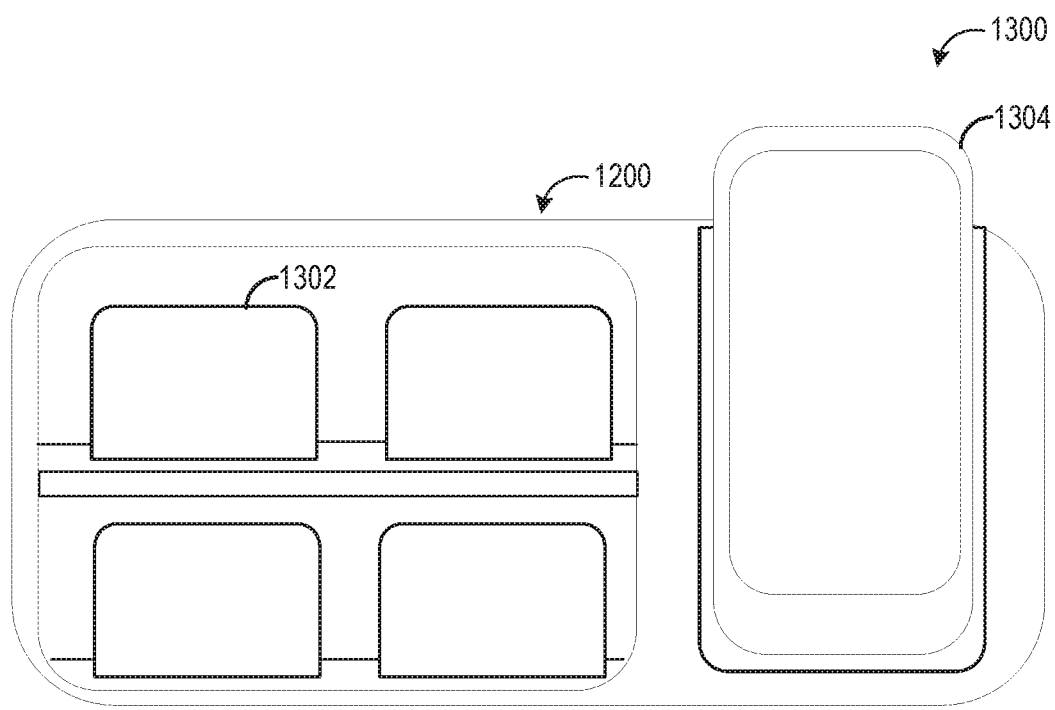
FIG. 13 shows the charging system of FIG. 12 charging a plurality of host devices and a patient monitoring hub.

FIG. 13 illustrates a configuration 1300 where the charging station of FIG. 12 is being used to charge a plurality of host devices and a patient monitoring hub. As shown, four host devices are connected to the charging station, including host device 1302. Further, a patient monitoring hub 1304 is connected to the charging station.

A technical effect of identifying that an associated component has been connected via a magnetic detection unit is that device connection may be confirmed before power is supplied, which may reduce the risk of current leakage. Another technical effect is that the presence and/or additional information of the associated component may be detected in a low-cost, low-power manner.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A host device, comprising:
   a connector configured to connect to a medical sensor device;
   a magnetic detection unit positioned proximate the connector and including a magnetic field generator and one or more magnetic field detectors; and
   a memory storing instructions executable by a processor to:
      determine a magnitude of a magnetic field generated by the magnetic field generator based on output from the one or more magnetic field detectors;
      in response to detecting a change in the magnitude of the magnetic field that is greater than a threshold change, establish a connection with the medical sensor device, the connection including a power connection; and
      determine a degradation state of the medical sensor device by entering the change in the magnitude of the magnetic field into a look up table stored in memory of the host device.

2. The host device of claim 1, wherein the host device further comprises a battery, wherein the connection with the medical sensor device further includes a data connection, wherein the data connection is a wired or wireless connection and the power connection is a wired or wireless connection.

3. The host device of claim 2, wherein establishing the connection with the medical sensor device comprises performing a handshake process with the medical sensor device responsive to detecting the change in the magnitude of the magnetic field that is greater than the threshold change.

4. The host device of claim 3, wherein the host device further includes a transceiver configured to transmit physiological data to a remote or proximate processing system.

5. The host device of claim 1, wherein the connector is configured to physically connect to a counterpart connector on the medical sensor device, the counterpart connector including a magnetizable part that induces the change in the magnetic field.

6. The host device of claim 5, wherein the medical sensor device includes a sensor for monitoring physiological conditions of a patient, the sensor comprising ECG electrodes, EEG electrodes, a blood pressure sensor, a temperature sensor, respiration rate electrodes, and/or a pulse oximeter.

7. The host device of claim 5, wherein the one or more magnetic field detectors comprise at least two magnetic field detectors, and wherein the magnetizable part is asymmetric in shape, thickness, and/or material properties to induce a spatially varying change in the magnetic field that is detected differentially by the at least two magnetic field detectors.

8. The host device of claim 7, wherein the instructions are executable to determine a respective change in the magnitude of the magnetic field for each magnetic field detector.

9. The host device of claim 1, wherein the instructions are executable to output a notification to a user responsive to determining the degradation state of the medical sensor device.

10. The host device of claim 1, wherein the connection with the medical sensor device includes a data connection, and wherein the instructions are executable to disable the power connection and data connection while maintaining a mechanical connection with the medical sensor device responsive to determining the degradation state of the medical sensor device.

11. A medical sensor device comprising:
    a sensor device; and
    a sensor for monitoring physiological conditions of a patient, the sensor removably attachable to the sensor device via a first connector of the sensor;
    a second connector of the sensor device configured to connect to a host device;
    a magnetizable part of the sensor positioned on or proximate to the first connector;
    a magnetic detection unit of the sensor device comprising a magnetic field generator and one or more magnetic field detectors; and
    a memory of the sensor device storing instructions executable by a processor to determine a magnitude of a magnetic field generated by the magnetic field generator based on output from the one or more magnetic field detectors, and in response to detecting a change in the magnitude of the magnetic field that is greater than a threshold change, establish at least a data connection with the sensor, wherein the magnetizable part has a form factor configured to induce a predefined change in the magnitude of the magnetic field, the form factor including the magnetizable part being asymmetric in shape, thickness, and/or material properties.

12. The medical sensor device of claim 11, wherein the magnetizable part is a first magnetizable part having a first form factor, and wherein the sensor device comprises a second magnetizable part having a second form factor configured to induce a predefined change in a magnitude of a magnetic field generated at the host device.

13. The medical sensor device of claim 11, wherein the instructions are further executable to determine a manufacturer of the sensor based on the output from the one or more magnetic field detectors, including entering the output from the one or more magnetic field detectors into a look-up table configured to output the manufacturer of the sensor.

14. The medical sensor device of claim 11, wherein the sensor comprises ECG electrodes, EEG electrodes, a blood pressure sensor, a temperature sensor, respiration rate electrodes, and/or a pulse oximeter, and wherein the magnetizable part is asymmetric in thickness.

15. The medical sensor device of claim 11, wherein the second connector includes a first connection point for receiving power from the host device and a second connection point for transferring data to and from the host device.

16. The medical sensor device of claim 11, wherein the magnetizable part is not permanently magnetized.

17. A method, comprising:
   generating, at a host device, an alternating magnetic field with a frequency of 1 Hz;
   detecting, at the host device, a change in the alternating magnetic field that is greater than a threshold change;
   responsive to detecting the change in the alternating magnetic field that is greater than the threshold change, supplying power via a power connection to a medical sensor device;
   receiving, at the host device, physiological data of a patient from the medical sensor device via a data connection with the medical sensor device; and
   transmitting, from the host device, the received physiological data to a patient monitoring hub.

18. The method of claim 17, wherein the physiological data of the patient is obtained by the medical sensor device via a sensor of the medical sensor device, and wherein the method further comprises:
   generating, at the medical sensor device, a second alternating magnetic field;
   detecting, at the medical sensor device, a change in the second magnetic field;
   identifying, based on the change in the second magnetic field, sensor information, the sensor information including a sensor type, a sensor manufacturer, a sensor degradation state, and/or a sensor orientation; and
   taking an action based on the sensor information, including outputting a notification indicating the sensor information, processing the physiological data based on the sensor information, and/or disabling the data connection, the power connection, and/or a connection between the sensor the medical sensor device.

* * * * *